(12) United States Patent
Ji

(10) Patent No.: US 7,405,062 B2
(45) Date of Patent: Jul. 29, 2008

(54) METHOD FOR CLONING VARIABLE DOMAIN SEQUENCES OF IMMUNOLOGICAL GENE REPERTOIRE

(75) Inventor: Henry Ji, San Diego, CA (US)

(73) Assignee: San Diego Antibody, San Diego, CA (US)

( * ) Notice: Subject to any disclaimer, the term of this patent is extended or adjusted under 35 U.S.C. 154(b) by 342 days.

(21) Appl. No.: 10/477,907

(22) PCT Filed: May 14, 2002

(86) PCT No.: PCT/US02/15125

§ 371 (c)(1),
(2), (4) Date: Nov. 13, 2003

(87) PCT Pub. No.: WO02/092770

PCT Pub. Date: Nov. 21, 2002

(65) Prior Publication Data

US 2004/0157210 A1    Aug. 12, 2004

(51) Int. Cl.
*C12P 19/34* (2006.01)
*C12Q 1/68* (2006.01)

(52) U.S. Cl. .......................... 435/91.2; 435/6
(58) Field of Classification Search ................ None
See application file for complete search history.

(56) References Cited

U.S. PATENT DOCUMENTS

| 5,554,516 | A | * | 9/1996 | Kacian et al. | ............ 435/91.21 |
| 5,627,052 | A | * | 5/1997 | Schrader | .................... 435/69.6 |
| 5,667,988 | A | * | 9/1997 | Barbas et al. | ............... 435/69.1 |
| 5,965,408 | A | * | 10/1999 | Short | ........................ 435/91.1 |

* cited by examiner

*Primary Examiner*—Young J. Kim
(74) *Attorney, Agent, or Firm*—Townsend and Townsend and Crew

(57) ABSTRACT

The present invention relates to a non-PCR (polymerase chain reaction) process, particularly a transcription-based amplification method, for amplifying and cloning sequences containing a variable domain sequence such as an immunoglobulin variable domain sequence from the immunological gene repertoire. The present invention comtemplates the expression of antibody library in either in an in vivo expression vector or in an in vitro transcription/translation system. Isolation of a gene coding for a receptor having the ability to bind a preselected ligand and receptors produced by the gene isolated by the method is also contemplated.

18 Claims, 10 Drawing Sheets

SEQUENCE LISTING

<160> NUMBER OF SEQ ID NOS: 58

<210> SEQ ID NO 1
<211> LENGTH: 5
<212> TYPE: PRT
<213> ORGANISM: Artificial Sequence
<220> FEATURE:

```
<223> OTHER INFORMATION: Linker peptide

<400> SEQUENCE: 1

Gly Gly Gly Gly Ser
1               5

<210> SEQ ID NO 2
<211> LENGTH: 33
<212> TYPE: DNA
<213> ORGANISM: Artificial Sequence
<220> FEATURE:
<223> OTHER INFORMATION: T7 RNA promoter sequence

<400> SEQUENCE: 2
ccagtgaatt gtaatacgac tcactatagg gaa                              33

<210> SEQ ID NO 3
<211> LENGTH: 42
<212> TYPE: DNA
<213> ORGANISM: Artificial Sequence
<220> FEATURE:
<223> OTHER INFORMATION: Antisense EcoRI & Stop Codon-Linked HJH primer

<400> SEQUENCE: 3
tggaatgaat tcgattgcta gtcagacggt gaccagggtg cc                    42

<210> SEQ ID NO 4
<211> LENGTH: 42
<212> TYPE: DNA
<213> ORGANISM: Artificial Sequence
<220> FEATURE:
<223> OTHER INFORMATION: Antisense EcoRI & Stop Codon-Linked HJH primer

<400> SEQUENCE: 4
tggaatgaat tcgattgcta gtcagacggt gaccattgtc cc                    42

<210> SEQ ID NO 5
<211> LENGTH: 42
<212> TYPE: DNA
<213> ORGANISM: Artificial Sequence
<220> FEATURE:
<223> OTHER INFORMATION: Antisense EcoRI & Stop Codon-Linked HJH primer

<400> SEQUENCE: 5
tggaatgaat tcgattgcta gtcagacggt gaccagggtt cc                    42

<210> SEQ ID NO 6
<211> LENGTH: 42
<212> TYPE: DNA
<213> ORGANISM: Artificial Sequence
<220> FEATURE:
<223> OTHER INFORMATION: Antisense EcoRI & Stop Codon-Linked HJH primer

<400> SEQUENCE: 6
tggaatgaat tcgattgcta gtcagacggt gaccgtggtc cc                    42

<210> SEQ ID NO 7
<211> LENGTH: 61
<212> TYPE: DNA
<213> ORGANISM: Artificial Sequence
<220> FEATURE:
<223> OTHER INFORMATION: Sense T7 & Not I-linked primer

<400> SEQUENCE: 7
ccagtgaatt gtaatacgac tcactatagg gaacggcatg gaatgcggcc gcccccccc  60
```

```
c                                                              61

<210> SEQ ID NO 8
<211> LENGTH: 72
<212> TYPE: DNA
<213> ORGANISM: Artificial Sequence
<220> FEATURE:
<223> OTHER INFORMATION: T7 & Peptide Linker(PL)-Linked Antisense HJH
      primer

<400> SEQUENCE: 8
ccagtgaatt gtaatacgac tcactatagg gaaagagccg ccgccgcctg aggagacggt    60
gaccagggtg cc                                                       72

<210> SEQ ID NO 9
<211> LENGTH: 72
<212> TYPE: DNA
<213> ORGANISM: Artificial Sequence
<220> FEATURE:
<223> OTHER INFORMATION: T7 & Peptide Linker(PL)-Linked Antisense HJH
      primer

<400> SEQUENCE: 9
ccagtgaatt gtaatacgac tcactatagg gaaagagccg ccgccgcctg aggagacggt    60
gaccattgtc cc                                                       72

<210> SEQ ID NO 10
<211> LENGTH: 72
<212> TYPE: DNA
<213> ORGANISM: Artificial Sequence
<220> FEATURE:
<223> OTHER INFORMATION: T7 & Peptide Linker(PL)-Linked Antisense HJH
      primer

<400> SEQUENCE: 10
ccagtgaatt gtaatacgac tcactatagg gaaagagccg ccgccgcctg aggagacggt    60
gaccagggtt cc                                                       72

<210> SEQ ID NO 11
<211> LENGTH: 72
<212> TYPE: DNA
<213> ORGANISM: Artificial Sequence
<220> FEATURE:
<223> OTHER INFORMATION: T7 & Peptide Linker(PL)-Linked Antisense HJH
      primer

<400> SEQUENCE: 11
ccagtgaatt gtaatacgac tcactatagg gaaagagccg ccgccgcctg aggagacggt    60
gaccgtggtc cc                                                       72

<210> SEQ ID NO 12
<211> LENGTH: 38
<212> TYPE: DNA
<213> ORGANISM: Artificial Sequence
<220> FEATURE:
<223> OTHER INFORMATION: Sense HVH primer
<220> FEATURE:
<221> NAME/KEY: misc_feature
<222> LOCATION: (21)..(21)
<223> OTHER INFORMATION: a or g or c or t/u

<400> SEQUENCE: 12
cagccggcca tggcacaggt ncagctggtr cagtctgg                           38
```

<210> SEQ ID NO 13
<211> LENGTH: 40
<212> TYPE: DNA
<213> ORGANISM: Artificial Sequence
<220> FEATURE:
<223> OTHER INFORMATION: Sense HVH primer

<400> SEQUENCE: 13
cagccggcca tggcacaggt ccagctggtr cagtctgggg                40

<210> SEQ ID NO 14
<211> LENGTH: 39
<212> TYPE: DNA
<213> ORGANISM: Artificial Sequence
<220> FEATURE:
<223> OTHER INFORMATION: Sense HVH primer

<400> SEQUENCE: 14
cagccggcca tggcacaggt kcagctggtg sagtctggg                 39

<210> SEQ ID NO 15
<211> LENGTH: 41
<212> TYPE: DNA
<213> ORGANISM: Artificial Sequence
<220> FEATURE:
<223> OTHER INFORMATION: Sense HVH primer

<400> SEQUENCE: 15
cagccggcca tggcacaggt caccttgarg gagtctggtc c              41

<210> SEQ ID NO 16
<211> LENGTH: 38
<212> TYPE: DNA
<213> ORGANISM: Artificial Sequence
<220> FEATURE:
<223> OTHER INFORMATION: Sense HVH primer

<400> SEQUENCE: 16
cagccggcca tggcacaggt gcagctggtg gagwctgg                  38

<210> SEQ ID NO 17
<211> LENGTH: 38
<212> TYPE: DNA
<213> ORGANISM: Artificial Sequence
<220> FEATURE:
<223> OTHER INFORMATION: Sense HVH primer

<400> SEQUENCE: 17
cagccggcca tggcacaggt gcagctggtg sagtcygg                  38

<210> SEQ ID NO 18
<211> LENGTH: 37
<212> TYPE: DNA
<213> ORGANISM: Artificial Sequence
<220> FEATURE:
<223> OTHER INFORMATION: Sense HVH primer

<400> SEQUENCE: 18
cagccggcca tggcacaggt gcagctgcag gagtcgg                   37

<210> SEQ ID NO 19
<211> LENGTH: 37
<212> TYPE: DNA
<213> ORGANISM: Artificial Sequence
<220> FEATURE:
<223> OTHER INFORMATION: Sense HVH primer

<400> SEQUENCE: 19
cagccggcca tggcacaggt gcagctgttg sagtctg          37

<210> SEQ ID NO 20
<211> LENGTH: 37
<212> TYPE: DNA
<213> ORGANISM: Artificial Sequence
<220> FEATURE:
<223> OTHER INFORMATION: Sense HVH primer

<400> SEQUENCE: 20
cagccggcca tggcacaggt gcagctggtg caatctg          37

<210> SEQ ID NO 21
<211> LENGTH: 38
<212> TYPE: DNA
<213> ORGANISM: Artificial Sequence
<220> FEATURE:
<223> OTHER INFORMATION: Sense HVH primer

<400> SEQUENCE: 21
cagccggcca tggcacaggt gcagctgcag gagtccgg         38

<210> SEQ ID NO 22
<211> LENGTH: 37
<212> TYPE: DNA
<213> ORGANISM: Artificial Sequence
<220> FEATURE:
<223> OTHER INFORMATION: Sense HVH primer

<400> SEQUENCE: 22
cagccggcca tggcacaggt gcagctacag cagtggg         37

<210> SEQ ID NO 23
<211> LENGTH: 37
<212> TYPE: DNA
<213> ORGANISM: Artificial Sequence
<220> FEATURE:
<223> OTHER INFORMATION: Sense HVH primer

<400> SEQUENCE: 23
cagccggcca tggcacaggt acagctgcag cagtcag         37

<210> SEQ ID NO 24
<211> LENGTH: 48
<212> TYPE: DNA
<213> ORGANISM: Artificial Sequence
<220> FEATURE:
<223> OTHER INFORMATION: Antisense Xhol & Stop Codon-Linked HJK primer

<400> SEQUENCE: 24
tggaattctc gagattgcta gtcaacgttt gatttccacc ttggtccc      48

<210> SEQ ID NO 25
<211> LENGTH: 48
<212> TYPE: DNA
<213> ORGANISM: Artificial Sequence
<220> FEATURE:
<223> OTHER INFORMATION: Antisense Xhol & Stop Codon-Linked HJK primer

<400> SEQUENCE: 25
tggaattctc gagattgcta gtcaactttt gatctccagc ttggtccc      48

<210> SEQ ID NO 26
<211> LENGTH: 48

```
<212> TYPE: DNA
<213> ORGANISM: Artificial Sequence
<220> FEATURE:
<223> OTHER INFORMATION: Antisense XhoI & Stop Codon-Linked HJK primer

<400> SEQUENCE: 26
tggaattctc gagattgcta gtcaacgttt gatatccact ttggtccc          48

<210> SEQ ID NO 27
<211> LENGTH: 48
<212> TYPE: DNA
<213> ORGANISM: Artificial Sequence
<220> FEATURE:
<223> OTHER INFORMATION: Antisense XhoI & Stop Codon-Linked HJK primer

<400> SEQUENCE: 27
tggaattctc gagattgcta gtcaacgttt gatctccacc ttggtccc          48

<210> SEQ ID NO 28
<211> LENGTH: 48
<212> TYPE: DNA
<213> ORGANISM: Artificial Sequence
<220> FEATURE:
<223> OTHER INFORMATION: Antisense XhoI & Stop Codon-Linked HJK primer

<400> SEQUENCE: 28
tggaattctc gagattgcta gtcaacgttt aatctccagt cgtgtccc          48

<210> SEQ ID NO 29
<211> LENGTH: 59
<212> TYPE: DNA
<213> ORGANISM: Artificial Sequence
<220> FEATURE:
<223> OTHER INFORMATION: Sense T7 & EcoRI-linked primer

<400> SEQUENCE: 29
ccagtgaatt gtaatacgac tcactatagg gaacggcatg gaatgaattc cccccccc          59

<210> SEQ ID NO 30
<211> LENGTH: 78
<212> TYPE: DNA
<213> ORGANISM: Artificial Sequence
<220> FEATURE:
<223> OTHER INFORMATION: T7-Linked Antisense HJk primer

<400> SEQUENCE: 30
ccagtgaatt gtaatacgac tcactatagg gaatggaatt cggcccccga ggccacgttt          60
gatttccacc ttggtccc                                                        78

<210> SEQ ID NO 31
<211> LENGTH: 78
<212> TYPE: DNA
<213> ORGANISM: Artificial Sequence
<220> FEATURE:
<223> OTHER INFORMATION: T7-Linked Antisense HJk primer

<400> SEQUENCE: 31
ccagtgaatt gtaatacgac tcactatagg gaatggaatt cggcccccga ggccacgttt          60
gatctccagc ttggtccc                                                        78

<210> SEQ ID NO 32
<211> LENGTH: 78
<212> TYPE: DNA
<213> ORGANISM: Artificial Sequence
<220> FEATURE:
```

<223> OTHER INFORMATION: T7-Linked Antisense HJk primer

<400> SEQUENCE: 32

```
ccagtgaatt gtaatacgac tcactatagg gaatggaatt cggcccccga ggccacgttt    60
gatatccact ttggtccc                                                  78
```

<210> SEQ ID NO 33
<211> LENGTH: 78
<212> TYPE: DNA
<213> ORGANISM: Artificial Sequence
<220> FEATURE:
<223> OTHER INFORMATION: T7-Linked Antisense HJk primer

<400> SEQUENCE: 33

```
ccagtgaatt gtaatacgac tcactatagg gaatggaatt cggcccccga ggccacgttt    60
gatctccacc ttggtccc                                                  78
```

<210> SEQ ID NO 34
<211> LENGTH: 78
<212> TYPE: DNA
<213> ORGANISM: Artificial Sequence
<220> FEATURE:
<223> OTHER INFORMATION: T7-Linked Antisense HJk primer

<400> SEQUENCE: 34

```
ccagtgaatt gtaatacgac tcactatagg gaatggaatt cggcccccga ggccacgttt    60
aatctccagt cgtgtccc                                                  78
```

<210> SEQ ID NO 35
<211> LENGTH: 74
<212> TYPE: DNA
<213> ORGANISM: Artificial Sequence
<220> FEATURE:
<223> OTHER INFORMATION: Sense Peptide Linker-Linked HVK-specific Primer

<400> SEQUENCE: 35

```
tcctcaggcg gcggcggctc tggcggaggt ggcagcggcg gtggcggatc cgacatccag    60
atgacccagt ctcc                                                      74
```

<210> SEQ ID NO 36
<211> LENGTH: 74
<212> TYPE: DNA
<213> ORGANISM: Artificial Sequence
<220> FEATURE:
<223> OTHER INFORMATION: Sense Peptide Linker-Linked HVK-specific Primer

<400> SEQUENCE: 36

```
tcctcaggcg gcggcggctc tggcggaggt ggcagcggcg gtggcggatc cgatgttgtg    60
atgactcagt ctcc                                                      74
```

<210> SEQ ID NO 37
<211> LENGTH: 74
<212> TYPE: DNA
<213> ORGANISM: Artificial Sequence
<220> FEATURE:
<223> OTHER INFORMATION: Sense Peptide Linker-Linked HVK-specific Primer

<400> SEQUENCE: 37

```
tcctcaggcg gcggcggctc tggcggaggt ggcagcggcg gtggcggatc cgaaattgtg    60
ttgacgcagt ctcc                                                      74
```

<210> SEQ ID NO 38
<211> LENGTH: 74
<212> TYPE: DNA
<213> ORGANISM: Artificial Sequence
<220> FEATURE:
<223> OTHER INFORMATION: Sense Peptide Linker-Linked HVK-specific Primer

<400> SEQUENCE: 38
tcctcaggcg gcggcggctc tggcggaggt ggcagcggcg gtggcggatc cgacatcgtg    60
atgacccagt ctcc                                                      74

<210> SEQ ID NO 39
<211> LENGTH: 74
<212> TYPE: DNA
<213> ORGANISM: Artificial Sequence
<220> FEATURE:
<223> OTHER INFORMATION: Sense Peptide Linker-Linked HVK-specific Primer

<400> SEQUENCE: 39
tcctcaggcg gcggcggctc tggcggaggt ggcagcggcg gtggcggatc cgaaacgaca    60
ctcacgcagt ctcc                                                      74

<210> SEQ ID NO 40
<211> LENGTH: 74
<212> TYPE: DNA
<213> ORGANISM: Artificial Sequence
<220> FEATURE:
<223> OTHER INFORMATION: Sense Peptide Linker-Linked HVK-specific Primer

<400> SEQUENCE: 40
tcctcaggcg gcggcggctc tggcggaggt ggcagcggcg gtggcggatc cgaaattgtg    60
ctgactcagt ctcc                                                      74

<210> SEQ ID NO 41
<211> LENGTH: 48
<212> TYPE: DNA
<213> ORGANISM: Artificial Sequence
<220> FEATURE:
<223> OTHER INFORMATION: Antisense XhoI & Stop Codon-Linked HJgamma
      Primer

<400> SEQUENCE: 41
tggaattctc gagattgcta gtcaacctag gacggtgacc ttggtccc                 48

<210> SEQ ID NO 42
<211> LENGTH: 48
<212> TYPE: DNA
<213> ORGANISM: Artificial Sequence
<220> FEATURE:
<223> OTHER INFORMATION: Antisense XhoI & Stop Codon-Linked HJgamma
      Primer

<400> SEQUENCE: 42
tggaattctc gagattgcta gtcaacctag gacggtcagc ttggtccc                 48

<210> SEQ ID NO 43
<211> LENGTH: 48
<212> TYPE: DNA
<213> ORGANISM: Artificial Sequence
<220> FEATURE:
<223> OTHER INFORMATION: Antisense XhoI & Stop Codon-Linked HJgamma
      Primer

<400> SEQUENCE: 43
tggaattctc gagattgcta gtcaacctaa aacggtgagc tgggtccc                 48

```
<210> SEQ ID NO 44
<211> LENGTH: 59
<212> TYPE: DNA
<213> ORGANISM: Artificial Sequence
<220> FEATURE:
<223> OTHER INFORMATION: Sense T7 & CcoRI-linked Primer

<400> SEQUENCE: 44
ccagtgaatt gtaatacgac tcactatagg gaacggcatg gaatgaattc cccccccc          59

<210> SEQ ID NO 45
<211> LENGTH: 78
<212> TYPE: DNA
<213> ORGANISM: Artificial Sequence
<220> FEATURE:
<223> OTHER INFORMATION: T7-Linked Antisense HJgamma Primer

<400> SEQUENCE: 45
ccagtgaatt gtaatacgac tcactatagg gaatggaatt cggcccccga ggccacctag        60
gacggtgacc ttggtccc                                                     78

<210> SEQ ID NO 46
<211> LENGTH: 78
<212> TYPE: DNA
<213> ORGANISM: Artificial Sequence
<220> FEATURE:
<223> OTHER INFORMATION: T7-Linked Antisense HJgamma Primer

<400> SEQUENCE: 46
ccagtgaatt gtaatacgac tcactatagg gaatggaatt cggcccccga ggccacctag        60
gacggtcagc ttggtccc                                                     78

<210> SEQ ID NO 47
<211> LENGTH: 78
<212> TYPE: DNA
<213> ORGANISM: Artificial Sequence
<220> FEATURE:
<223> OTHER INFORMATION: T7-Linked Antisense HJgamma Primer

<400> SEQUENCE: 47
ccagtgaatt gtaatacgac tcactatagg gaatggaatt cggcccccga ggccacctaa        60
aacggtgagc tgggtccc                                                     78

<210> SEQ ID NO 48
<211> LENGTH: 74
<212> TYPE: DNA
<213> ORGANISM: Artificial Sequence
<220> FEATURE:
<223> OTHER INFORMATION: Sense Peptide Linker-Linked HVgamma Specific
      Primer

<400> SEQUENCE: 48
tcctcaggcg gcggcggctc tggcggaggt ggcagcggcg gtggcggatc ccagtctgtg        60
ttgacgcagc cgcc                                                         74

<210> SEQ ID NO 49
<211> LENGTH: 74
<212> TYPE: DNA
<213> ORGANISM: Artificial Sequence
<220> FEATURE:
<223> OTHER INFORMATION: Sense Peptide Linker-Linked HVgamma Specific
      Primer
```

-continued

```
<400> SEQUENCE: 49
tcctcaggcg gcggcggctc tggcggaggt ggcagcggcg gtggcggatc ccagtctgcc    60
ctgactcagc ctgc                                                      74

<210> SEQ ID NO 50
<211> LENGTH: 74
<212> TYPE: DNA
<213> ORGANISM: Artificial Sequence
<220> FEATURE:
<223> OTHER INFORMATION: Sense Peptide Linker-Linked HVgamma Specific
      Primer

<400> SEQUENCE: 50
tcctcaggcg gcggcggctc tggcggaggt ggcagcggcg gtggcggatc ctcctatgtg    60
ctgactcagc cacc                                                      74

<210> SEQ ID NO 51
<211> LENGTH: 74
<212> TYPE: DNA
<213> ORGANISM: Artificial Sequence
<220> FEATURE:
<223> OTHER INFORMATION: Sense Peptide Linker-Linked HVgamma Specific
      Primer

<400> SEQUENCE: 51
tcctcaggcg gcggcggctc tggcggaggt ggcagcggcg gtggcggatc ctcttctgag    60
ctgactcagg accc                                                      74

<210> SEQ ID NO 52
<211> LENGTH: 74
<212> TYPE: DNA
<213> ORGANISM: Artificial Sequence
<220> FEATURE:
<223> OTHER INFORMATION: Sense Peptide Linker-Linked HVgamma Specific
      Primer

<400> SEQUENCE: 52
tcctcaggcg gcggcggctc tggcggaggt ggcagcggcg gtggcggatc ccacgttata    60
ctgactcaac cgcc                                                      74

<210> SEQ ID NO 53
<211> LENGTH: 74
<212> TYPE: DNA
<213> ORGANISM: Artificial Sequence
<220> FEATURE:
<223> OTHER INFORMATION: Sense Peptide Linker-Linked HVgamma Specific
      Primer

<400> SEQUENCE: 53
tcctcaggcg gcggcggctc tggcggaggt ggcagcggcg gtggcggatc ccaggctgtg    60
ctcactcagc cgtc                                                      74

<210> SEQ ID NO 54
<211> LENGTH: 74
<212> TYPE: DNA
<213> ORGANISM: Artificial Sequence
<220> FEATURE:
<223> OTHER INFORMATION: Sense Peptide Linker-Linked HVgamma Specific
      Primer

<400> SEQUENCE: 54
tcctcaggcg gcggcggctc tggcggaggt ggcagcggcg gtggcggatc caattttatg    60
```

-continued

```
ctgactcagc ccca                                                    74

<210> SEQ ID NO 55
<211> LENGTH: 38
<212> TYPE: DNA
<213> ORGANISM: Artificial Sequence
<220> FEATURE:
<223> OTHER INFORMATION: Sense Sfi scFv Primer

<400> SEQUENCE: 55
ttgttattac tcgcggccca gccggccatg gcacaggt                          38

<210> SEQ ID NO 56
<211> LENGTH: 35
<212> TYPE: DNA
<213> ORGANISM: Artificial Sequence
<220> FEATURE:
<223> OTHER INFORMATION: Antisense Sfi scFv Primer

<400> SEQUENCE: 56
gtcctcgtcg actggaattc ggcccccgag gccac                             35

<210> SEQ ID NO 57
<211> LENGTH: 61
<212> TYPE: DNA
<213> ORGANISM: Artificial Sequence
<220> FEATURE:
<223> OTHER INFORMATION: Sense T7 & NotI-linked Primer

<400> SEQUENCE: 57
ccagtgaatt gtaatacgac tcactatagg aacggcatg gaatgcggcc gcccccccc    60 c                                                                  61

<210> SEQ ID NO 58
<211> LENGTH: 44
<212> TYPE: DNA
<213> ORGANISM: Artificial Sequence
<220> FEATURE:
<223> OTHER INFORMATION: Sense Peptide Linker-Linked HVK-specific Primer

<400> SEQUENCE: 58
ggcagcggcg gtggcggatc cgaaattgtg ctgactcagt ctcc                   44
```

METHOD FOR CLONING VARIABLE DOMAIN SEQUENCES OF IMMUNOLOGICAL GENE REPERTOIRE

TECHNICAL FIELD

The present invention relates to methods for amplifying and cloning variable region or domain sequences of the immunological genes, generating libraries of immunological gene repertoire and isolating a gene coding for an antigen-combining molecule such as antibody or immunoglobulin.

BACKGROUND

A dozen or so monoclonal antibodies have been approved by the Food and Drug Administration (FDA) as human therapeutics including Orthoclone OKT3 for allograft rejection, ReoPro (abciximab) for adjunct treatment of percutaneous coronary intervention (PCI) including balloon angioplasty, atherectomy and stent placement, Rituxan for Non-Hodgkin's lymphoma, Simulet and Zenapax for organ rejection prophylaxis, Remicade for Rheumatoid arthritis and Crohn's disease, Synagis for respiratory syncytial virus (RSV), Herceptin for metastatic breast cancer, Mylotarg for acute myeloid leukemia and Campath for chronic lymphocytic leukemia, etc. These therapeutic antibodies can be divided into three major categories: murine monoclonal antibodies (Orthoclone OKT3); chimeric monoclonal antibodies (ReoPro, Rituxan, Simulet, and Remicade); and CDR-grafted monoclonal antibodies (Zenapax, Synagis, Herceptin, Mylotarg, and Campath). A murine monoclonal antibody is a mouse antibody; a chimeric antibody contains antibody of two or more species of animal, such as human and mouse; while CDR-grafted antibodies have lower amounts of foreign protein, generally in the complementarity determining region (CDR), thus the framework is human and the CDR are of mouse origin. In the above clinically approved antibodies, the non-human portion of the antibody derived is from a mouse antibody.

The mouse portion of the murine, chimeric or even CDR-grafted antibodies would elicit an immune response and associated side effects when administrated to a human, such as HAMA (human anti-mouse antibody) or HACA (human anti-chimeric antibody) responses. Thus, therapeutic antibody development is best suited with totally or 100% human antibodies.

There are two approaches in making human antibodies. One approach uses a human-mouse system such as the XenoMouse technology of Abgenix (Fremont, Calif.) or the HuAbMouse technology of Medarex, Inc. (Princeton, N.J.), wherein the host mouse immunoglobulin genes are inactivated and most of the human immunoglobulin genes are incorporated into the mouse to produce totally human antibodies in response to antigen stimuli in the mouse. Some of the difficulties in producing monoclonal antibodies with the human-mouse methodology include genetic instability, smaller antigenic specificities due to tolerance restriction of certain antibodies in a live animal, low throughput in access and screening of the in vivo antibody repertoire which can only be accessed via immunization with a selection on the basis of binding affinity and low production capacity.

The other approach is to generate libraries of antibody genes by cloning. Often the target genes are amplified prior to cloning.

There are a number of methods in the field of amplifying specific target nucleic acid sequences of interest. The polymerase chain reaction method (PCR), as described by Mullis et al., (see U.S. Pat. Nos. 4,683,195, 4,683,202, and 4,800,159; and European Patent Application Nos. 86302298.4, 86302299.2, and 87300203.4, and Methods in Enzymology, Volume 155, 1987, pp. 335-350), is one of the most prominent methods. PCR involves the use of a pair of specific oligonucleotides as primers for the two complementary strands of the double-stranded DNA containing the target sequence. The primers are chosen to hybridize at the ends of each of the complementary target strands, 3' of the target sequence. Template-dependent DNA synthesis, on each strand, can then be catalyzed using a thermostable DNA polymerase in the presence of the appropriate reagents. A thermal cycling process is required to form specific hybrids prior to synthesis and then to denature the double stranded nucleic acid formed by synthesis. Repeating the cycling process geometrically amplifies the target sequence.

A PCR method employing a reverse transcription step is also used with an RNA target using RNA-dependent DNA polymerase to create a DNA template. The PCR method has been coupled to RNA transcription by incorporating a promoter sequence into one of the primers used in the PCR reaction and then, after amplification by the PCR method, using the double-stranded DNA as a template for the transcription of single-stranded RNA. (see, e.g., Murakawa et al., DNA 7:287-295 (1988)). The PCR method has been applied to the amplification and cloning of the variable domain sequences of immunoglobulin or antibody genes (U.S. Pat. No. 6,291,158 to Winter et al. and U.S. Pat. No. 6,291,161 to Lerner et al.).

There are, however, several non-PCR-based amplification methods that can be used for amplifying specific target genes. One types of the non-PCR-based amplification methods include multiple cycles of DNA-dependent RNA polymerase-driven RNA transcription amplification or RNA-directed DNA synthesis and transcription to amplify DNA or RNA targets (see, e.g., Burg et al., WO 89/01050; Gingeras et al., WO 88/10315; Kacian and Fultz, EPO Application No. 89313154; Davey and Malek, EPO Application No. 88113948.9; Malek et al., WO91/02818 and U.S. Pat. No. 5,130,238; Davey et al., U.S. Pat. Nos. 5,409,818; 5,466,586; 5,554,517 and 6,063,603; Eberwine et al., U.S. Pat. No. 5,514,545; Lin et al., U.S. Pat. No. 6,197,554; and Kacian et al., U.S. Pat. No. 5,888,779).

Another type of amplification method uses a ligase chain reaction (LCR) as described in European Patent Publication No. 320,308. This method requires at least four separate oligonucleotides, two of which hybridize to the same nucleic acid template so their respective 3' and 5' ends are juxtaposed for ligation. The hybridized oligonucleotides are then ligated forming a complementary strand on the nucleic acid template. The double-stranded nucleic acid is then denatured, and the third and fourth oligonucleotides are hybridized with the first and second oligonucleotides that were joined together. The third and fourth oligonucleotides are then ligated together. Amplification is achieved by further cycles of hybridization, ligation, and denaturation.

Another amplification method uses Qβ replicase (Qβ) method as described in PCT Publication Ser. No. 87/06270 and U.S. Pat. No. 4,786,600 that uses a specific RNA probe which is capable of specific transcription by a replicase enzyme. The method requires the design and synthesis of RNA probes with replicase initiation sites.

Another type of amplification uses palindromic probes as described in EPO Publication Nos. 0427073A and 0427074A. The palindromic probe forms a hairpin with a nucleic acid target sequence. The probe contains a functional promoter located in the hairpin region from which RNA transcripts are produced.

There are also several versions of a strand displacement amplification method that uses one strand of DNA to displace same strand DNA sequences hybridized to their complementary DNA sequences to generate many copies of the target DNA sequences under isothermal conditions.

Walker et al., Proc. Natl. Acad. Sci. U.S.A., 89:392-396 (January 1992), Walker et al., Nucl. Acids Res. 20:1691-1696 (1992), European Patent Application No. EP 0 497272, and European Patent Application No. EP 0 500 224, describe an oligonucleotide-driven amplification method using a restriction endonuclease. The restriction endonuclease nicks the DNA/DNA complex to enable an extension reaction and, therefore, amplification.

Becker et al., EPO Application No. 88306717.5, describe an amplification method in which a primer is hybridized to a nucleic acid sequence and the resulting duplex cleaved prior to the extension reaction and amplification.

Dattagupta et al. described another version of the strand displacement amplification method by using a nucleic acid polymerase lacking 5' exonuclease activity and a set of oligonucleotide primers to carry out isothermal amplification without requiring exonuclease activity or restriction endonuclease activity (U.S. Pat. No. 6,214,587).

Another amplification method is rolling circle amplification. The method involves insertion of a nucleic acid molecule of interest in a linear vector to form a circular vector where one strand is continuous and the other strand is discontinuous. The continuous strand of the circular vector is then amplified by rolling circle replication, amplifying the inserted nucleic acid molecule in the process. The amplification is rapid and efficient since it involves a single, isothermal reaction that replicates the vector sequences exponentially (U.S. Pat. No. 6,287,824 to Lizardi).

A related amplification method using a similar approach is termed ramification extension amplification (RAM), U.S. Pat. No. 5,942,391 to Zhang et al. The RAM method involves hybridizing a target nucleic acid to several non-overlapping oligonucleotide probes that hybridize to adjacent regions in the target nucleic acid, the probes being referred to as capture/amplification probes and amplification probes, respectively, in the presence of paramagnetic beads coated with a ligand binding moiety. Through the binding of a ligand attached to one end of the capture/amplification probe and the specific hybridization of portions of the probes to adjacent sequences in the target nucleic acid, a complex comprising the target nucleic acid, the probes and the paramagnetic beads is formed. The probes may then ligate together to form a contiguous ligated amplification sequence bound to the beads, which complex may be denatured to remove the target nucleic acid and unligated probes.

Attempts to clone variable domain sequences of the immunological genes into an antibody framework vector and expressing the antibodies in a host cell such as in a phage using PCR have been described (U.S. Pat. No. 6,291,158 to Winter, et al.; and U.S. Pat. No. 6,291,161 to Lerner, et al.). Some of the difficulties in employing that PCR amplification scheme are that PCR amplification efficiency is dependent on both the primer and the template sequences. Certain sequences are preferentially amplified with other sequences being under-amplified or not amplified leading to under representation of the diversity of the resulting antibody libraries. An example of the limitations encountered when using PCR to clone a library is provided in Gao et al., Proc. Natl. Acad. Sci. (1999) 96:6025-6030.

The size of the human antibody repertoire is estimated to be on the order of $10^6$ to $10^8$ different antigen specificities. Exceptional larger numbers of specificities of the human antibodies can be generated by in vitro construction of $V_H$ and/or $V_L$ libraries by random recombination and shuffling, and saturation mutagenesis of the $V_H$ and $V_L$ DNA homologs.

One of the potential benefits of constructing human antibody libraries is to obviate the need for immunization by the generation of highly diverse "generic" human antibody libraries. In certain cases, very specialized human antibody libraries such as human antibody libraries made by using blood cells of cancer patients or blood cells of patients with autoimmune diseases such as rheumatoid arthritis, psoriasis, etc. may contain human antibodies with very high avidity and specificity for that particular diseases. Another benefit of having human antibody libraries is that they permit iterative cycles of mutagenesis or random recombination of the $V_H$ and $V_L$ gene repertoire to further optimize the specificity, affinity or catalytic properties of the immunoglobulins or their derivative antibodies such as $F_{ab}$ and $scF_v$ fragments.

BRIEF SUMMARY OF THE INVENTION

The present invention relates to methods for amplifying and cloning variable region or domain sequences of immunological genes, generating libraries of immunological gene repertoire and isolating a gene coding for an antigen-combining molecule such as antibody or immunoglobulin. The present invention employs a non-PCR amplification process such as DNA-dependent RNA polymerase driven RNA transcription-based amplification methods, strand displacement amplification methods, ligase chain reaction, rolling circle amplification, ramification amplification methods, and replicase driven amplification methods.

The present invention specifically contemplates and details a transcription-based amplification scheme for amplifying and cloning sequences containing a sequence encoding a variable domain sequence such as an immunoglobulin variable domain sequence. The transcription-based amplification (TCA) process is based on transcriptional amplification by DNA-dependent RNA polymerase from DNA sequences containing a promoter sequence for the binding of RNA polymerase and the initiation of RNA transcription activity as shown in FIG. 1. Unlike the two-fold per cycle amplification rate of a PCR-based reaction, the RNA polymerase driven RNA transcription based amplification process provides up to, per one round of RNA transcription, two thousand-fold amplification of the desired starting materials, especially to the immunoglobulin variable domain sequences. Following TCA, the resulting double stranded DNA is cloned in a suitable vector. That process non-selectively, outside of the specificity imposed by the primers, which are of design choice and based on the molecules to be cloned, amplifies all suitable target sequences thereby enriching rare targets or targets generally unsuitable for amplification and cloning using other amplification methods and ensuring suitable levels of target for cloning.

The advantages of using RNA transcriptional amplification rather than PCR amplification are: firstly, single copy messenger RNA (mRNA) can be increased up to 2000-fold in one round of amplification with proofreading activity. Secondly, the RNA transcriptional amplification is linear and does not result in preferential amplification, which is a major problem associated with PCR-based amplification reactions. Thirdly, the RNA transcriptional amplification process can be applied to amplify multiple sequences simultaneously with a capacity of amplifying at least more than ten to twenty sequences at a time in a single reaction, while the PCR-based amplification has limited ability for multiplexing with a typical limit of amplifying less than ten, most often less than five sequences in a single group reaction (Gao et al., supra). The RNA transcriptional amplification method has often been used to amplify or to reproduce the entire mRNA transcriptome from a single neuron cell or 20 to 50 cancer cells. (Lin et al., Nucl. Acids Res. 27:4585-4598, 1999). Also, the resulting amplified mRNA products, in some cases full-length sequences, can be used for further peptide/protein synthesis directly in an in vitro transcription/translation system such as the PROfusion and the ribosome display technologies as further discussed below in the present invention.

One can use the RNA transcriptional amplification process to transcriptionally amplify the mRNA transcripts of a gene family by more than one billion-fold and subject the resultant amplified mRNA transcripts of the gene family directly to translation into peptide/protein products in vitro or in vivo for antigen-antibody related applications. Alternatively, one can convert the amplified mRNAs into double-stranded cDNAs with appropriate restriction enzyme sites for further cloning into an expression-competent vector in a host cell, such as in a phage display system.

The present invention provides a novel non-PCR-based amplification method for amplifying and cloning a larger population of the immunological repertoire for immunoglobulin genes and receptors having a preselected activity against immunogens, ligands, small molecules or macromolecules, thereby overcoming the before-mentioned inadequacies of preferential amplification of the PCR-based amplification technique.

In one embodiment, a gene library is generated or synthesized for the immunoglobulin light kappa chain variable region ($V_K$) gene repertoire of a vertebrate such as a human being. In preferred embodiments, the $V_K$ gene library contains at least about $10^3$, preferably at least about $10^4$, more preferably at least about $10^5$, and most preferably at least about $10^6$ different $V_K$ DNA homologs, although higher diversity amounts of $10^7$-$10^{11}$ clones are possible because of the library properties inherent when using filamentous phage.

Methods for evaluating the diversity of a gene repertoire are well known to one skilled in the art.

The $V_K$ gene library can be synthesized by either of two methods, depending on the starting material, mRNAs or genomic DNAs.

In one embodiment, the mRNAs of a tissue or cell of immune system origin, such as blood cells, are used as the source of immunological genes. The mRNAs of the immunoglobulin genes are reversed transcribed by specific $V_K$ antisense primers operatively linked with a promoter sequence for a DNA-dependent RNA polymerase such as T7 promoter (the RNA promoter-linked primer). The RNA promoter-linked primer for the $V_K$ genes is situated in the conserved region adjacent to the variable domain of the $V_K$ genes, such as the J region in the constant region of the kappa light chain. The resulting cDNAs are made into double-stranded (ds) cDNAs by double stranding reactions with sense $V_K$ primers situated in the relatively conserved region in the variable region of the $V_K$ genes. The ds cDNAs are then transcribed by the DNA-dependent RNA polymerase such as T7 polymerase into hundreds to thousands copies of antisense RNA transcripts. The amplified RNA transcripts can be amplified again. The antisense RNA transcripts are reverse transcribed into sense DNAs (sDNAs) by the sense $V_K$ primers, the single stranded sDNAs are made into ds DNAs with the RNA promoter-linked primers. The resulting ds DNAs can be tranerscribed into hundreds to thousands of copies of RNA transcripts again by the DNA-dependent RNA polymerase. With two rounds of transcription amplification, the original mRNAs of immunoglobulin genes are copied into hundreds of thousands to millions of copies of antisense RNA transcripts complementary to the original sequences. The above process can be repeated or cycled a few more times, if needed. The resulting RNA transcripts can be easily converted into ds DNAs by techniques known in the art and the resulting ds DNAs are ready for further cloning and/or expression of the antigen-combining molecules on in vitro transcription and translation or in an expression vector in a host cell such as a lambda phage.

In another embodiment, genomic DNAs from an immunological tissue or cells such as blood cells or other stimulated immunological cells with rearranged immunoglobulin genes, are used as the cloning source for the $V_K$ genes. The variable region of the immunoglobulin genes are copied only once into ds DNAs by the two primers as discussed in the previous embodiments, the ds DNAs are amplified by a similar RNA transcription based amplification process discussed in the previous embodiments and so on.

In another embodiment, a similar approach and method to the $V_K$ gene library cloning processes as discussed in the previous embodiments are employed to generate or to synthesize the immunoglobulin light chain lambda variable region ($V_\lambda$) gene repertoire of a vertebrate such as a human being. In preferred embodiments, the $V_\lambda$ gene library contains at least about $10^3$, preferably at least about $10^4$, more preferably at least about $10^5$, and most preferably at least $10^6$ different $V_\lambda$ DNA homologs, although higher diversity amounts of $10^7$ to about $10^{11}$ clones are possible because of the library properties inherent when using filamentous phage.

In another embodiment, a similar approach and method to the $V_K$ gene library cloning processes as discussed in the previous embodiments are employed to generate or synthesize the immunoglobulin heavy chain variable region ($V_H$) gene repertoire of a vertebrate such as a human being. In preferred embodiments, the $V_H$ gene library contains at least about $10^3$, preferably at least about $10^4$, more preferably at least about $10^5$, and most preferably at least $10^6$ different $V_H$ DNA homologs, although higher diversity amounts of $10^7$ to more than $10^{11}$ clones are possible because of the library properties inherent when using filamentous phage.

Additionally, the size and diversity of the library of proteins can be increased by introducing a modifying step wherein the nucleic acids are changed to yield new proteins. Those new proteins can yield proteins that have the same antigen specificity with the same or differing properties. For example, effector functions, such as binding and activating complement, can vary between the parent protein and the modified derivative protein. Alternatively, the modified proteins can have a different antigen specificity. Such modification can be obtained by mutagenesis, such as a generalized mutagenesis procedure, for example using terminal transferase, or a specific procedure such as site-directed mutagenesis.

For cloning and expression purposes, the antisense and sense primers described in the above embodiments are designed to have appropriate restriction enzyme digestion sites and are fused into appropriate expression vectors or in vitro transcription and translation framework sequences. The expression of the antigen-combining molecules can be achieved either via in vitro transcription and translation or by expression in a host cell through cloning in an expression vector as known in the art. For in vitro transcription and translation expression of the immunological genes, the primers are designed to fuse appropriately into a framework sequence, which contains sequences necessary for adequate coupling of in vitro transcription and translation utilizing methods known in the art.

The amplified sequences of the variable domains of the immunological genes such as immunoglobulin genes can be cloned into antibody framework vectors for expression in host cells such as lambda bacterial phage or mammalian cells. The sequences can also be inserted into antibody framework sequences useful for in vitro translation coupling with in vitro transcription. The framework sequences can be of antibody origin or other framework scaffold molecules useful in presenting antigen-combining activities of the antibody variable regions.

The variable domains of the immunoglobulin heavy chain $V_H$ and light chains $V_L$ ($V_K$ and $V_\lambda$) can be separately amplified and cloned, expressed and combined. Alternatively, the variable domains of the heavy and light chains of the immunoglobulins can be linked with a peptide linker to form single chain $F_v$ (sc$F_v$) or a single chain antibody.

An immunological receptor having a preselected activity, preferably catalytic activity, produced by a method of the present invention, preferably a $V_H$, $V_K$, $V_L$, $F_{ab}$ and/or sc$F_v$ as described herein, is also contemplated.

DETAILED DESCRIPTION OF THE INVENTION

Figure 1:
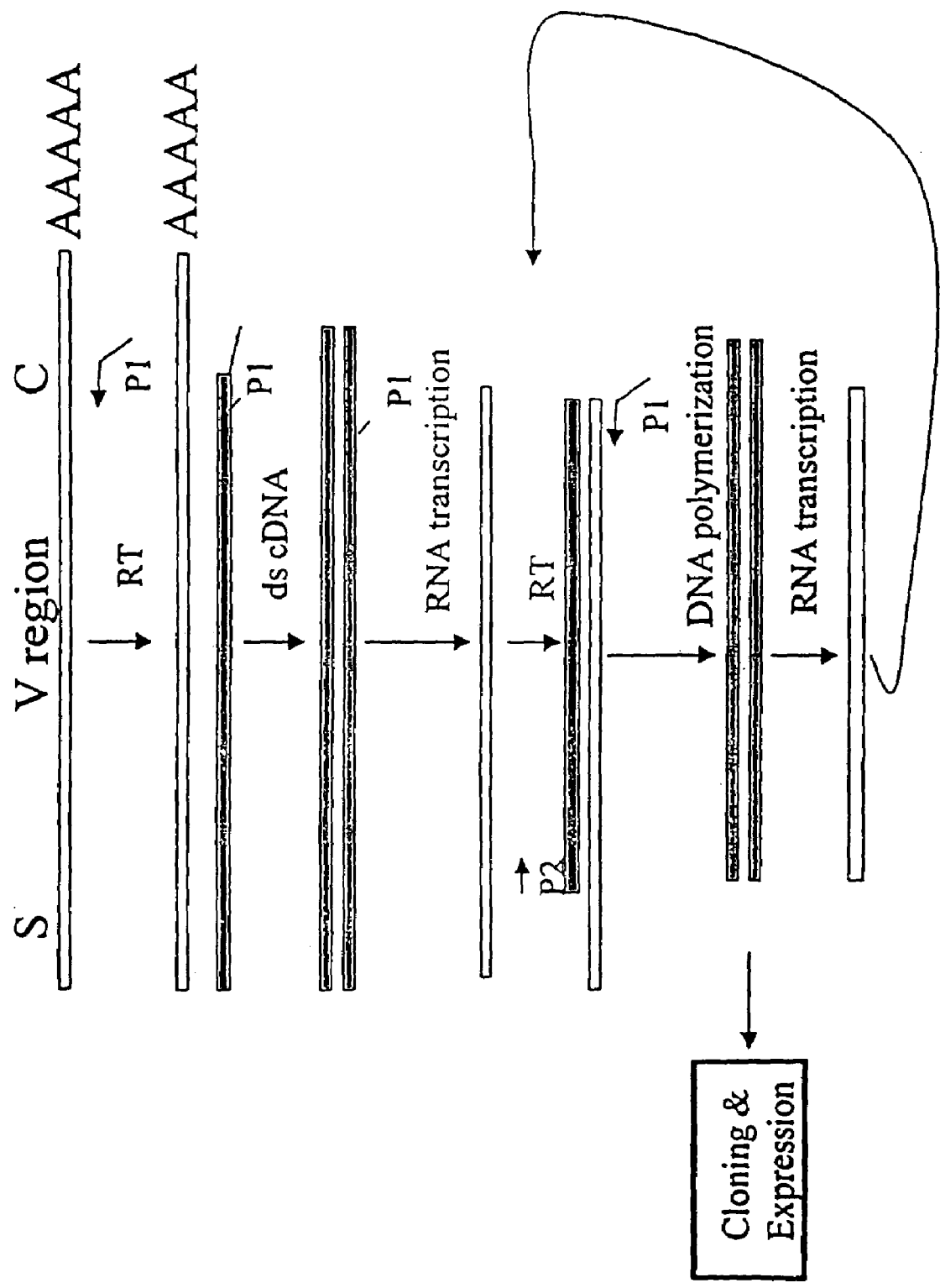
FIG. 1 illustrates a schematic representation of a general scheme of transcription based RNA amplification. Briefly, an antisense primer is used to reverse transcribe mRNA into cDNA using a reverse transcriptase. The ds cDNA contains the RNA promoter sequence and is transcribed into RNA transcripts by the RNA polymerase. The amplified RNA transcripts can be amplified again by repeating the process. The ds cDNAs with appropriate restriction enzyme sites can be cloned into appropriate expression vector or in vitro transcription/translation unit sequence for further expression in vivo or in vitro. The RNA promoter sequence can be linked either with the antisense primer or the sense primer. The RNA transcripts can be in sense orientation or antisense orientation dependent on whether the RNA promoter sequence is linked to the sense or antisense primer. An amplification scheme for amplifying the immunoglobulin gene variable regions using mRNAs as the source, employing antisense promoter-linked primers for reverse transcription and RNA transcription, and a strand separation to enable making the double stranded cDNA.

Referring to FIGS. 1 to 10, a novel method for cloning variable domain sequences of immunological gene repertorie of the present invention is illustrated, wherein open bars represent RNA and solid bars represent DNA.

A. Definitions

To facilitate understanding of the invention, a number of terms are defined below:

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide.

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding.

Nucleic Acid: a polymer of nucleotides, either single or double stranded.

Gene: a nucleic acid whose nucleotide sequence codes for an RNA or a polypeptide. A gene can be either RNA or DNA.

cDNA: a single stranded DNA that is homologous to an mRNA sequence and does not contain any intronic sequences.

Sense: a nucleic acid molecule in the same sequence order and composition as the homolog mRNA. The sense conformation is indicated with a "+", "s" or "sense" symbol.

Antisense: a nucleic acid molecule complementary to the respective mRNA molecule. The antisense conformation is indicated as a "−" symbol or with a "a" or "antisense" in front of the DNA or RNA, e.g., "aDNA" or "aRNA".

Template: a nucleic acid molecule being copied by a nucleic acid polymerase. A template can be single-stranded, double-stranded or partially double-stranded, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA molecule, double stranded RNA molecule, hybrid molecules such as DNA-RNA or RNA-DNA hybrid, or single-stranded DNA or RNA molecule.

Oligonucleotide: a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Primer: an oligonucleotide complementary to a template. The primer complexes with the template to yield a primer/template duplex for initiation of synthesis by a DNA polymerase. The primer/template complex is extended during DNA synthesis by the addition of covalently bonded bases linked at the 3' end, which are complementary to the template. The result is a primer extension product. Virtually all known DNA polymerases (including reverse transcriptases) require complexing of an oligonucleotide to a single-stranded template ("priming") to initiate DNA synthesis. A primer is selected to be "substantially" or "sufficiently" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template/primer complex for synthesis of the extension product of the primer.

Complementary or Complementarity or Complementation: used in reference to polynucleotides (i.e., a sequence of nucleotides) related by the base-pairing rules. For example, the sequence "A-G-T" is complementary to the sequence "T-C-A," and also to "T-C-U." Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Homologous or homology: refers to a polynucleotide sequence having similarities with a gene or mRNA sequence. A nucleic acid sequence may be partially or completely homologous to a particular gene or mRNA sequence, for example. Homology may also be expressed as a percentage determined by the number of similar nucleotides over the total number of nucleotides.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Conserved: a nucleotide sequence is conserved with respect to a preselected (reference) sequence if it non-randomly hybridizes to an exact or total complement of the preselected sequence.

Hybridize and Hybridization: the formation of complexes between nucleotide sequences which are sufficiently complementary to form complexes via complementary base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotide that can be competitively inhibited.

Nucleotide Analog: a purine or pyrimidine nucleotide that differs structurally from T, G, C, or U, but is sufficiently similar to substitute for the normal nucleotide in a nucleic acid molecule.

DNA Homolog: a nucleic acid having a preselected conserved nucleotide sequence and a sequence coding for a receptor capable of binding a preselected ligand.

Promoter-Linked Primer: an RNA-polymerase-promoter sense sequence coupled with a gene-specific complementary sequence in its 3' portion for annealing to the antisense conformation of a nucleic acid template.

Amplification: nucleic acid replication involving template specificity. Template specificity is frequently described in terms of "target" specificity. Target sequences are "targets" in that they are sought to be sorted out from other nucleic acids. Amplification techniques have been designed primarily for this sorting. Template specificity is achieved in most amplification techniques by the choice of enzyme. Amplification enzymes are enzymes that will process only specific sequences of nucleic acid in a heterogeneous mixture of nucleic acids. For example, in the case of Qβ replicase, MDV-1 RNA is the specific template for the replicase (Kacian et al. (1972) Proc. Natl. Acad. Sci. USA 69, 3038). Other nucleic acid will not be replicated by this amplification enzyme. Similarly, T7 RNA polymerase has a stringent specificity for its own promoters (Chamberlin et al. (1970) Nature 228, 227). Taq and Pfu polymerases, by virtue of their ability to function at high temperature, display high specificity for the sequences bonded, and thus defined by the primers.

Enzymatic Amplification: (such as PCR, NASBA and RNA-PCR): a method for increasing the concentration of a segment in a target sequence from a mixture of nucleic acids without cloning or purification (U.S. Pat. Nos. 4,683,195; 4,683,202; 4,965,188 (PCR); U.S. Pat. No. 5,888,779 (NASBA); U.S. Pat. No. 6,197,554 (RNA-PCR) and WO 00/75356, hereby incorporated by reference). Amplification of the target sequence by PCR consists of introducing a large excess of two oligonucleotide primers to the DNA mixture containing the desired target sequence, followed by a precise sequence of thermal cycling in the presence of DNA and/or RNA polymerase(s). The two primers are complementary to their respective strands of the double stranded target sequence. To effect amplification, the mixture is denatured and the primers then annealed to complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. Because the desired amplified segments of the target sequence become the predominant sequences (in terms of concentration) in the mixture, they are said to be amplified. With enzymatic amplification, it is possible to amplify a single copy of a specific target sequence in genomic DNA to a level detectable by several different methodologies (e.g., incorporation of biotinylated primers followed by avidin-enzyme conjugate detection; incorporation of $^{32}$P labeled triphosphates, such as dCTP or dATP, into the amplified segment). In addition to genomic DNA, any oligonucleotide or polynucleotide sequence can be amplified with the appropriate set of primer molecules. In particular, the amplified segments created by the PCR and RNA-PCR process itself are, themselves, efficient templates for subsequent PCR and RNA-PCR amplification.

Polymerase Chain Reaction (PCR): an amplification reaction is typically carried out by cycling i.e., simultaneously performing in one admixture, the first and second primer extension reactions, each cycle comprising polynucleotide synthesis followed by denaturation of the double stranded polynucleotides formed. Methods and systems for amplifying a DNA homolog are described in U.S. Pat. Nos. 4,683,195 and 4,683,202, both to Mullis et al.

Amplifiable Nucleic Acid and Amplified Products: nucleic acids that may be amplified by any amplification method.

DNA-dependent DNA Polymerase: an enzyme that synthesizes a complementary DNA copy from a DNA template. Examples are DNA polymerase I from *E. coli* and bacteriophage T7 DNA polymerase. Under suitable conditions a DNA-dependent DNA polymerase may synthesize a complementary DNA copy from an RNA template.

DNA-dependent RNA Polymerase or Transcriptase: enzymes that synthesize multiple RNA copies from a double stranded or partially double stranded DNA molecule having a promoter sequence. Examples of transcriptases include, but are not limited to, DNA-dependent RNA polymerase from *E. coli* and bacteriophage T7, T3, and SP6.

RNA-dependent DNA Polymerase or Reverse Transcriptase: enzymes that synthesize a complementary DNA copy from an RNA template. All known reverse transcriptases also have the ability to make a complementary DNA copy from a DNA template. Thus, reverse transcriptases are both RNA-dependent and DNA-dependent DNA polymerases.

RNase H: an enzyme that degrades the RNA portion of an RNA/DNA duplex. RNase H may be an endonuclease or an exonuclease. Most reverse transcriptase enzymes normally contain an RNase H activity. However, other sources of RNase H are available, without an associated polymerase activity. The degradation may result in separation of the RNA from a RNA/DNA complex. Alternatively, the RNase H may simply cut the RNA at various locations such that pieces of the RNA melt off or are susceptible to enzymes that unwind portions of the RNA.

Reverse Transcription: the synthesis of a DNA molecule from an RNA molecule using an enzymatic reaction in vitro. For example, the RNA molecule may be primed with a primer that is complementary to the RNA molecule and the DNA molecule is synthesized by extension using a reverse transcriptase such as Tth DNA polymerase with reverse transcription activity, MMLV reverse transcriptase, AMV reverse transcriptase, and any other enzyme that has the ability to synthesize a DNA molecule from an RNA molecule template.

In Vitro Transcription: the synthesis of an RNA molecule from a DNA molecule using an enzymatic reaction in vitro. For example, the DNA molecule may be double stranded and comprises an RNA polymerase promoter such as T7, SP6, T3, or any other enzyme promoter for synthesis of RNA from DNA.

Vector: a recombinant nucleic acid molecule such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and/or expression of nucleic acids to which they are linked. Vectors capable of directing the expression of genes encoding for one or more polypeptides are referred to herein as "expression vectors". Particularly important vectors allow cloning of cDNA from mRNAs produced using a reverse transcriptase.

In Vitro Transcrintion/Translation Unit: a polynucleotide sequence comprising all the necessary nucleic acid sequence elements for operably linking a desired nucleic acid sequence and regulatory elements for in vitro transcription and optionally translation reactions for expressing the operably inserted nucleic acid sequence into an mRNA and optionally a polypeptide in an in vitro system without a host cell.

Functional parts: a portion of an intact molecule that retains one or more desired properties of the intact molecules. Thus, for example, an antibody binds an antigen. In that context of the property of binding that antigen, a functional part of an antibody can be any portion of an antibody that binds the cognate antigen. Similarly, a functional part of a nucleic acid that encodes an antibody that binds that antigen is any portion of that nucleic acid that encodes a polypeptide that binds to that antigen.

Receptor: a molecule, such as a protein, glycoprotein and the like, that can specifically (non-randomly) bind to another molecule. An antibody is an example of a receptor.

Antibody: in various grammatical forms as used herein refers to immunoglobulin molecules and immunologically active portions of immunoglobulin molecules, i.e., molecules that contain a combining site for antigen or paratope. Exemplary antibody molecules are intact immunoglobulin molecules, substantially intact immunoglobulin molecules and portions of an immunoglobulin molecules, including those portions known in the art as $F_{ab}$, $F_{ab'}$, $(F_{ab'})_2$, $F_v$, and $scF_v$.

Antibody Combining Site: an antibody combining site is that structural portion of an antibody molecule comprised of a heavy and light chain variable and hypervariable regions that specifically binds (immunoreacts with) an antigen.

Immunoreact: in various forms means specific binding between an antigenic determinant-containing molecule and a molecule containing an antibody combining site such as a whole antibody molecule or a portion thereof.

Fusion Polypeptide: a polypeptide comprised of at least two polypeptides and optionally a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

Cistron: a sequence of nucleotides in a DNA molecule coding for an amino acid residue sequence and including upstream and downstream DNA expression control elements.

Promoter: a nucleic acid to which a polymerase molecule recognizes, perhaps binds to, and initiates synthesis. For the purposes of the instant invention, a promoter can be a known polymerase binding site, an enhancer and the like, any sequence that can initiate synthesis by a desired polymerase.

Replicase: an RNA-dependent RNA polymerase such as Brome mosaic virus replicase, togaviridae virus replicase, Flock house virus replicase and Qβ replicase.

Rearranged B cells: B cells in which immunoglobulin gene translocation, i.e., rearrangement, has occurred as evidenced by the presence in the cell of mRNA with the immunoglobulin gene V, D and J region transcripts adjacently located thereon.

B. Methods

The present invention provides a novel method for amplifying and cloning the variable regions of the immunoglobulin heavy ($V_H$) and light ($V_L$ of $V_K$ and $V_\lambda$) chains to generate a very diverse human antibody library representing the vast immunological repertoire. The $V_H$ and $V_L$ DNA homologs are further expressed in either separate forms for an antibody receptor heterodimeric molecule or as a fusion such as an $scF_v$ antibody, capable of binding a preselected ligand. Distinctively different from the PCR-based amplification method (U.S. Pat. No. 6,291,158 to Winter, et al.), the present invention generally uses non-PCR-based amplification methods, in specific, a transcription-based amplification (TCA) for amplifying the $V_H$ and $V_L$ DNA homologs. The DNA homologs of the amplified $V_H$ and $V_L$ are further cloned into framework expression vectors known in the art. Heterodimeric antibody receptor or single chain $scF_v$ antibodies are expressed either in a host cell or in an in vitro transcription and translation (TnT) system. The present invention combines the following elements as discussed in details thereafter:

1. isolation of nucleic acids (genomic DNAs or mRNAs) from immunological tissue or cell sources containing a substantial portion of the immunological repertoire;

2. preparation of oligonucleotide primers and promoter-linked primers for amplifying and cloning DNA homologs containing immunoglobulin $V_H$ and $V_L$ variable regions of the immunoglobulin heavy and light chain genes;

3. amplification and cloning of a gene library containing a substantial population of different $V_H$ and $V_L$ genes;

4a. in vivo expression of the $V_H$ and $V_L$ polypeptides in an appropriate host, including prokaryotic and eukaryotic hosts, either separately or in the same cell, either on the same or different expression vectors, and either in linked single chain ($scF_v$) form or separate heterodimeric receptor form; or alternatively, 4b. in vitro expression of the $V_H$ and $V_L$ polypeptides in an in vitro transcription and/or translation system, either in the same or different framework, and either in linked single chain ($scF_v$) form or in separate heterodimeric receptor form; and 5. screening the antibody library for antibodies with a preselected activity.

As generally known in the art, the composition and length of the $V_H$ and $V_L$ vary widely, depending on the particular idiotype involved. Typically, the individual $V_H$ and $V_L$ polypeptides have fewer than 125 amino acid residues, more usually between 60 to 120 amino acid residues. The $V_H$ polypeptides are often 110 to 125 amino acid residues in length while $V_L$ polypeptides are 95 to 115 amino acid residues in length. Usually, there are at least two cysteines separated by from about 60 to 75 amino acid residues and are joined by a disulfide bond. The $V_H$ and $V_L$ polypeptides produced by the subject invention will normally be substantial faithful copies of idiotypes of the variable regions of the heavy and/or light chains of immunoglobulins, however, these polypeptides can be further mutated by site-specific or random mutagenesis to advantageously improve the desired antigen-combining specificity and affinity. Typically the C terminus region of the $V_H$ and $V_L$ polypeptides would have a greater variety of the sequences than would the N terminus and, based on the present invention, can be further modified through either site directed or random mutagenesis to generate greater diversity than the normally occurring $V_H$ and $V_L$ polypeptides. A synthetic oligonucleotide can be employed to vary one or more amino acids in a hypervariable region of the $V_H$ and/or $V_L$ polypeptides.

A $V_H$ or $V_L$ polypeptide can be produced separately as two separate transcripts from a single or two different vectors by the subject invention and can be active in monomeric as well as multimeric forms, either homomeric or heteromeric, preferably heterodimeric. $V_H$ and $V_L$ polypeptides produced by the present invention can be advantageously combined in a heterodimeric antibody to offer unique antigen combining activities.

The present invention can produce also the $F_{ab}$ antibody as a heterodimer comprised of a $V_H$ polypeptide tagged with a portion of the heavy chain constant region and a $V_L$ polypeptide tagged with substantially all of the light chain constant region. The production of $F_{ab}$ can be advantageous in some situations because the additional constant region sequences contained in a $F_{ab}$ as compared to a $F_v$ could stabilize the $V_H$ and $V_L$ interactive conformation. Such stabilization may potentially increase the affinity of the $F_{ab}$ for corresponding antigen. In addition, the $F_{ab}$ is more commonly used in the art and thus there are more commercial antibodies available to specifically recognize an $F_{ab}$, especially to the constant regions of an $F_{ab}$.

Preferably the antibody produced by the subject invention is single chain or the $scF_v$ and is therefore normally comprised of the $V_H$ and $V_L$ linked with an artificial linker such as $G_4S$ or GlyGlyGlyGlySer(SEQ ID NO:1) linker peptide, or multiple copies of such a linker, such as $(G_4)_n$. The $V_H$ and $V_L$ portions bend together to assume a conformation having a binding affinity, or association constant for the preselected antibody that is different, preferably higher, than the affinity or association constant of either of the $V_H$ or $V_L$ polypeptides alone, i.e. as monomers. This single-chain antigen-binding antibody has been described by Bird et al., *Science*, 242:423-426 (1988). The design of suitable peptide linker regions is described in U.S. Pat. No. 4,704,692 by Robert Ladner. Such a peptide linker could be designed as part of the nucleic acid sequences contained in the expression vector or in the in vitro translation framework sequences. The nucleic acid sequences coding for the peptide linker would be between the $V_H$ and $V_L$ DNA homologs and the restriction endonuclease sites used to operatively link the $V_H$ and $V_L$ DNA homologs to the expression vector. Such a peptide linker could also be coded by nucleic acid sequences that are part of the oligonucleotide primers used to prepare the $V_H$ and $V_L$ gene libraries so that overlapping sequences can be fused to form the $scF_v$ DNA homologs for cloning into an appropriate expression vector or framework sequences.

An antibody produced by the present invention possesses a specific combining activity and conformation having a binding site specific for an antigen as evidenced by its ability to be competitively inhibited. In one embodiment, an antibody of this invention possesses an antigen-combining binding site and can be selected by the ability to specifically bind to a preselected antigen to form an immunoreaction product (complex) with a preselected antigen having a sufficiently strong binding between the antigen and the binding site for the immunoreaction product to be isolated. The antibody typically has an affinity or avidity that is generally greater than $10^5 M^{-1}$, more usually greater than $10^6$, and preferably greater than $10^8 M^{-1}$.

In another embodiment, an antibody produced by the subject invention possesses catalytic activities by binding to a substrate and catalyzing the formation of a product from the substrate. The topology or conformation of the ligand-combining site of a catalytic antibody is probably more important for the preselected catalytic activity than the affinity (association constant or $pK_a$) for the substrate. The subject catalytic antibodies are preferred to have an association constant for the preselected substrate generally greater than $10^3 M^{-1}$, more usually greater than $10^4 M^{-1}$ or $10^5 M^{-1}$, and preferably greater than $10^7 M^{-1}$.

1. Isolation of nucleic acids (genomic DNAs or mRNAs) from immunological tissue or cell sources containing a substantial portion of the immunological repertoire:

As a general rule, the preferred starting source materials or tissues (i.e. peripheral blood, bone marrow, spleen or regional lymph nodes) for the antibody repertoire include, but are not limited to, a heterogeneous population of antibody producing cells, i.e. B lymphocytes (B cells), preferably rearranged B cells such as those found in the circulation or spleen of a vertebrate. It is generally known in the art that the greater the genetic heterogeneity of the population of cells for which the source nucleic acids are obtained, the greater the diversity of the immunological repertoire that will be made available for screening. Preferably, blood cells from different individuals, particularly those having an immunologically significant age difference, and different races or species can be advantageously combined to increase the diversity of the repertoire.

In certain cases, it is desirable to enrich the immunoglobulin gene repertoire for antibodies with higher affinity to a preselected activity, such as by using as a source of blood cells (source cells) from cancer patients, patients with autoimmune diseases or people in any one of various stages of age, health and immune response or from animals through repeated immunization.

In one preferred embodiment, the source cells are obtained from pooled human blood cells of cancer patients with high affinity antibodies against specific cancer or cancers. In another embodiment, the source cells are obtained from pooled human blood cells of patients with autoimmune diseases such as rheumatoid arthritis, psoriasis, etc.

Nucleic acids such as genomic DNAs or mRNAs coding for $V_H$ and $V_L$ polypeptides can be derived from cells producing IgA, IgD, IgE, IgG or IgM, most preferably from IgM-producing cells and IgG-producing cells. The desired $V_H$ and $V_L$ gene repertoire can be isolated from either genomic DNA or the messenger RNA (mRNA) containing transcripts of the variable regions. It may be less desirable to use the genomic DNA from non-rearranged B lymphocytes, wherein the sequences coding for the variable region are juxtaposed or separated by intronic or intervening sequences. To be useful for making the $V_H$ and/or $V_L$ gene library, the DNA fragment(s) containing the proper exons of the variable regions must first be isolated, the introns excised, and the exons then spliced in the proper order and in the proper orientation. It is, however, relatively easier to use rearranged B cells as source materials for cloning the $V_H$ and $V_L$ regions because the C, D and J immunoglobulin gene regions have translocated to become adjacent and continuous (free of introns) for the entire variable regions.

Methods for preparing fragments of genomic DNA from which immunoglobulin heavy and light chain variable region genes can be amplified and cloned are well known in the art, see for example Herrmann et al., Methods In Enzymol., 152: 180-183, (1987); Frischauf, Methods In Enzymol., 152:183-190 (1987); Frischauf, Methods In Enzymol., 152:190-199 (1987); and DiLella et al., Methods In Enzymol., 152:199-212 (1987).

Methods for isolating mRNA from source cells are known in the art. The procedure typically comprises lysis of cells under RNase inhibiting conditions. In one embodiment, the total cellular mRNA is isolated by employing an oligo-dT cellulose column, see for example Sambrook et al., "Molecular Cloning, $2^{nd}$ ed.", Cold Spring Harbor Laboratory Press.

2. Preparation of oligonucleotide primers and promoter-linked primers for amplifying and cloning DNA homologs containing immunoglobulin $V_H$ and $V_L$ ($V_K$ and $V_\lambda$) variable regions of the immunoglobulin heavy and light chain genes.

The oligonucleotide primers and the gene-specific primer sequences of the promoter-linked primers used herein are selected to be "substantially" complementary to the different strands of each specific sequence to be synthesized or amplified. The primer so selected is sufficiently complementary to nonrandomly hybridize with the respective template strand. In the case of the promoter-linked primers, a non-complementary RNA promoter sequence is attached to the 5' end of the gene-specific primer, with the gene-specific primer sequence being substantially complementary to the strand for nonrandom hybridization. The oligonucleotide primer and/or the promoter-linked primer can also have noncomplementary fragments for an endonuclease restriction site for cloning purposes.

The selection of a gene-specific primer for the $V_H$ and $V_L$ ($V_K$ and $V_\lambda$) depends on various factors such as the distance on the nucleic acid from the region coding for the desired receptor, its hybridization site on the nucleic acid relative to any second primer to be used, the number of genes in the repertoire it is to hybridize to, and the like.

For example, to produce $V_H$ DNA homologs by the subject invention, the nucleotide sequence of a primer (including the primer segment of the promoter-linked primers) is selected to hybridize with a plurality of immunoglobulin heavy chain genes at a site substantially adjacent to the $V_H$ region so that a nucleotide sequence coding for a functional (capable of binding) polypeptide is obtained. To hybridize to a plurality of different $V_H$ nucleic acid strands, the primer must be a substantial complement of a nucleotide sequence conserved among the different strands. Such sites include nucleotide sequences in the constant region, any of the variable region framework regions, the third framework region, leader region, promoter region, J region and the like.

Figure 4:
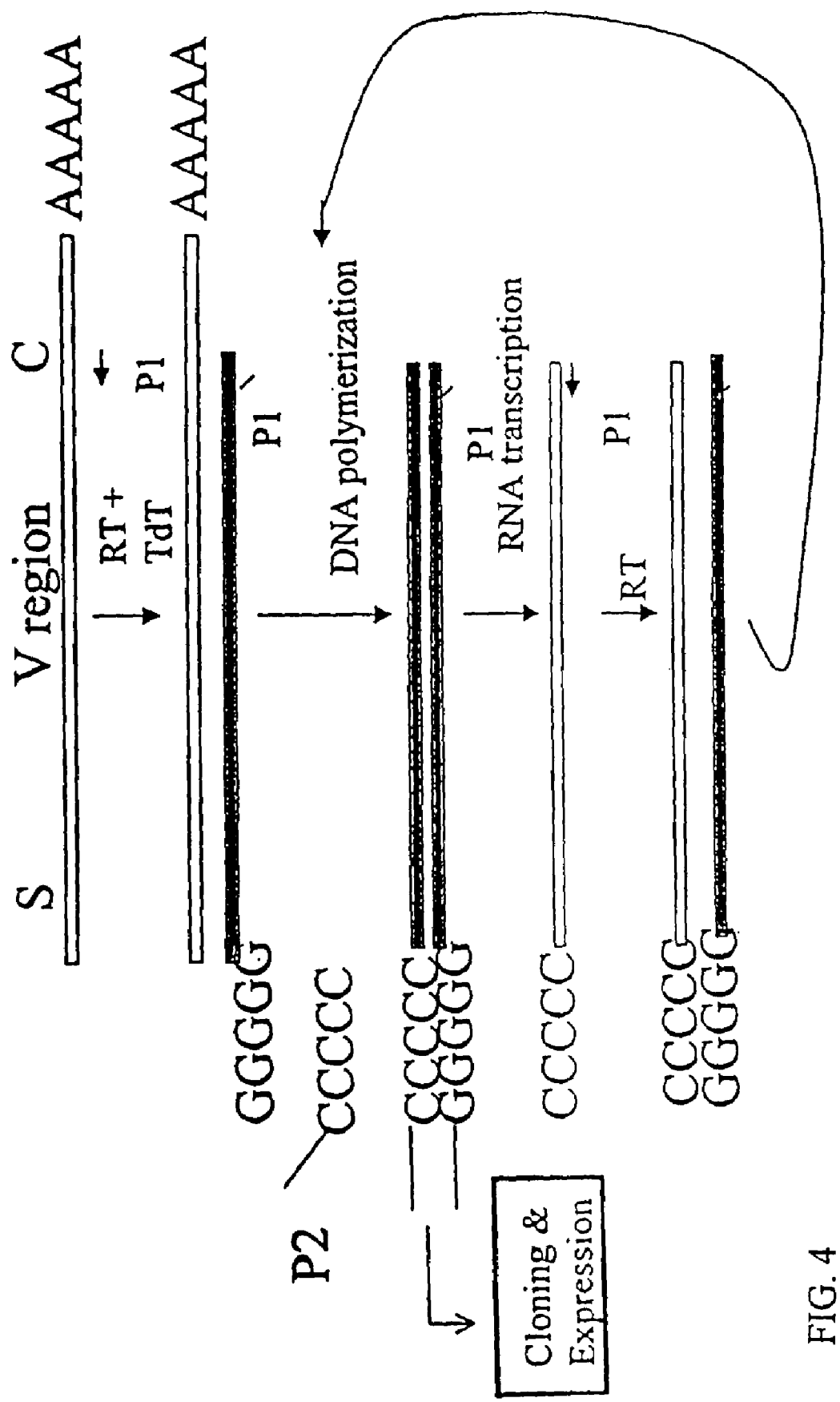
FIG. 4 illustrates a schematic diagram of another RNA transcription based amplification scheme for amplifying the immunoglobulin gene variable regions using mRNAs as the source, employing terminal transferase for oligonucleotide tailing, promoter-linked primers for double stranding and RNA transcription, and antisense primers for reverse transcription.

In the present invention, the $V_H$ and $V_L$ DNA homologs are produced by RNA transcription-based amplification. Two oligonucleotides, one gene-specific primer and one promoter-linked primer, which contains a gene specific primer and an RNA promoter sequence linked to the 5'-end of the gene-specific primer or the poly(dC)n oligonucleotide in the case of using a terminal tailing reaction as depicted in FIG. 4, can be used for each strand of nucleic acid to be amplified. The RNA promoter sequence can be linked to either the sense or the antisense primer to be the promoter-linked primer for RNA transcription. Table 1, Table 2 and Table 3 list sets of gene-specific primers for both the gene-specific primers and promoter-linked primers for $V_H$, $V_K$ and $V_\lambda$ with the T7 RNA promoter sequence linked with either the sense or antisense gene-specific primers.

The oligonucleotide primers and the promoter-linked primers can be prepared using any suitable method, such as, for example, the phosphotriester or phosphodiester methods see Narang et al., Meth. Enzymol., 68:90, (1979); U.S. Pat. No. 4,356,270; and Brown et al., Meth. Enzymol., 68:109, (1979).

3. Amplification and cloning of gene libraries containing a substantial population of different $V_H$ and/or $V_L$ genes will depend, as is well known in the art, on the type, complexity, and purity of the nucleic acids making up the input repertoire. Other factors include whether or not the genes are to be amplified and/or mutagenized. The amplification and cloning strategies of the present invention are dependent also on the input repertoire of the double stranded genomic DNA or the mRNA isolated from the source immunological cells, preferably the human blood cells.

Figure 2:
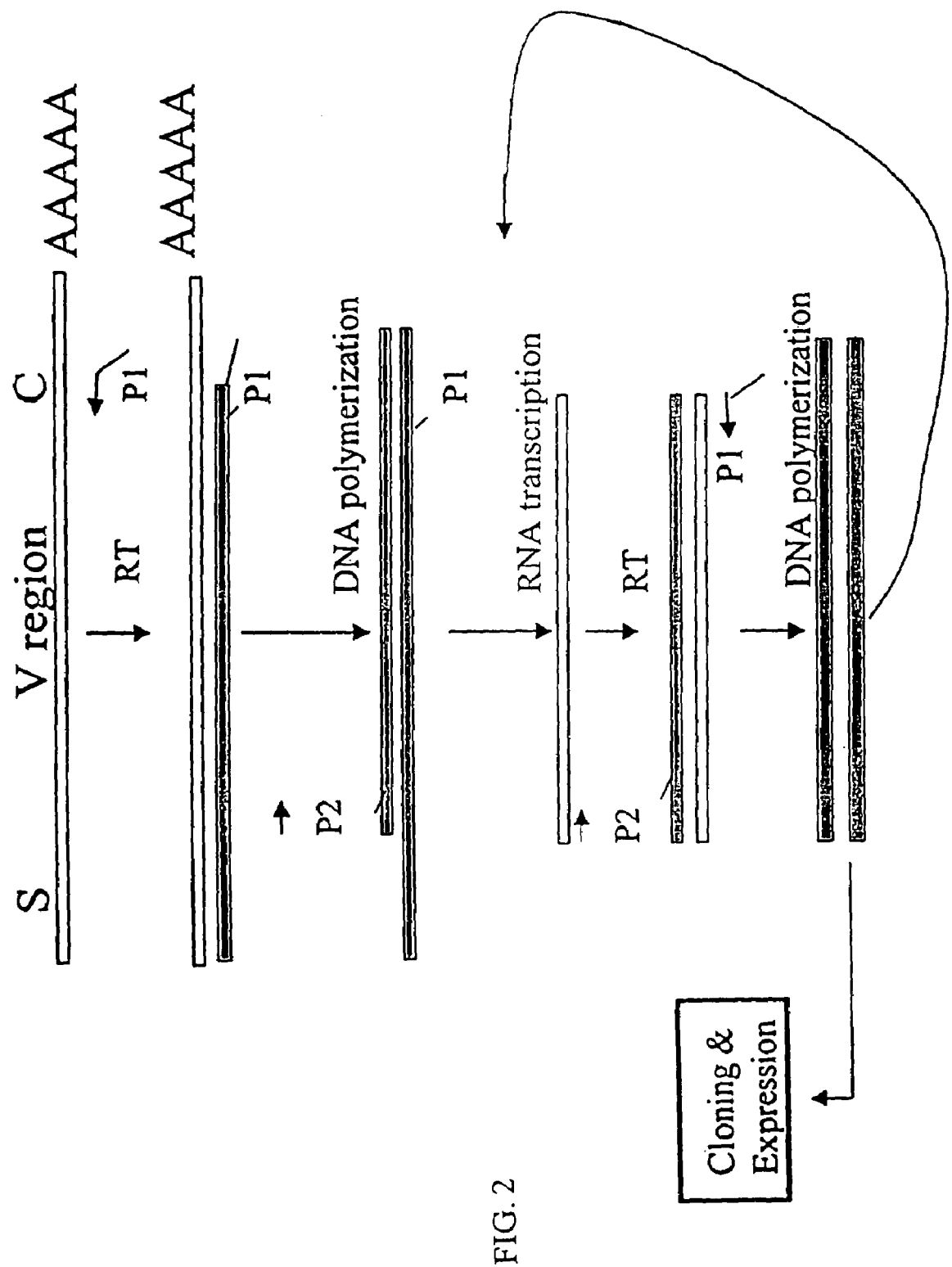
FIG. 2 illustrates a schematic diagram of another RNA transcription based amplification scheme for amplifying the immunoglobulin gene variable regions using mRNAs as a source, employing antisense promoter-linked primers for reverse transcription and RNA transcription, and a sense gene-specific primer extension based double stranding scheme for making double stranded cDNA.

In one embodiment, the isolated mRNAs of a tissue or cells of immunological origin are the source materials for the immunoglobulin gene repertoire. As depicted in FIG. 1, the mRNAs of the immunoglobulin genes can be reversed transcribed using an antisense gene-specific primer linked with the RNA promoter sequence for a DNA-dependent RNA polymerase such as the T7 promoter (the promoter-linked primer, P1). The P1 primer is situated in the conserved region adjacent to the variable domain such as in the J regions of the heavy or light chains. The resulting cDNAs are made into double-stranded (ds) cDNAs by methods known in the art, such as using the RNA priming with RNase H treatment as depicted in FIG. 1 or by priming with a sense gene-specific primer (P2) situated in the relatively conserved region of the $V_H$ or $V_L$ as depicted in FIG. 2. In both embodiments of FIGS. 2 and 3, the ds cDNAs are then transcribed by the DNA-dependent RNA polymerase, such as T7 polymerase, into up to 2,000 copies of antisense RNA transcripts. The amplified antisense RNA transcripts can be amplified again. The antisense RNA transcripts are reverse transcribed into sense DNAs (sDNAs) by a reverse transcriptase using a sense P2 primer, the single-stranded sDNAs are made into ds DNAs with the P1 primer of the promoter-linked primer. The resulting ds DNAs can be transcribed into up to 2,000 copies of antisense RNA transcripts again by the DNA-dependent RNA polymerase. With two cycles of transcription amplification, the original mRNAs of the $V_H$ or $V_L$ gene repertoire are amplified or reproduced by hundreds of thousands to millions fold of antisense RNA transcripts complementary to the original mRNA sequences. The above process can be repeated or cycled a couple of more times, if needed. The resulting antisense RNA transcripts can be readily converted into clonable ds DNAs by techniques known in the art and the resulting clonable ds $V_H$ and $V_L$ DNA homologs are ready for further cloning and/or expression in in vitro transcription and/or translation systems or in an in vivo expression vector in a host cell.

Figure 3:
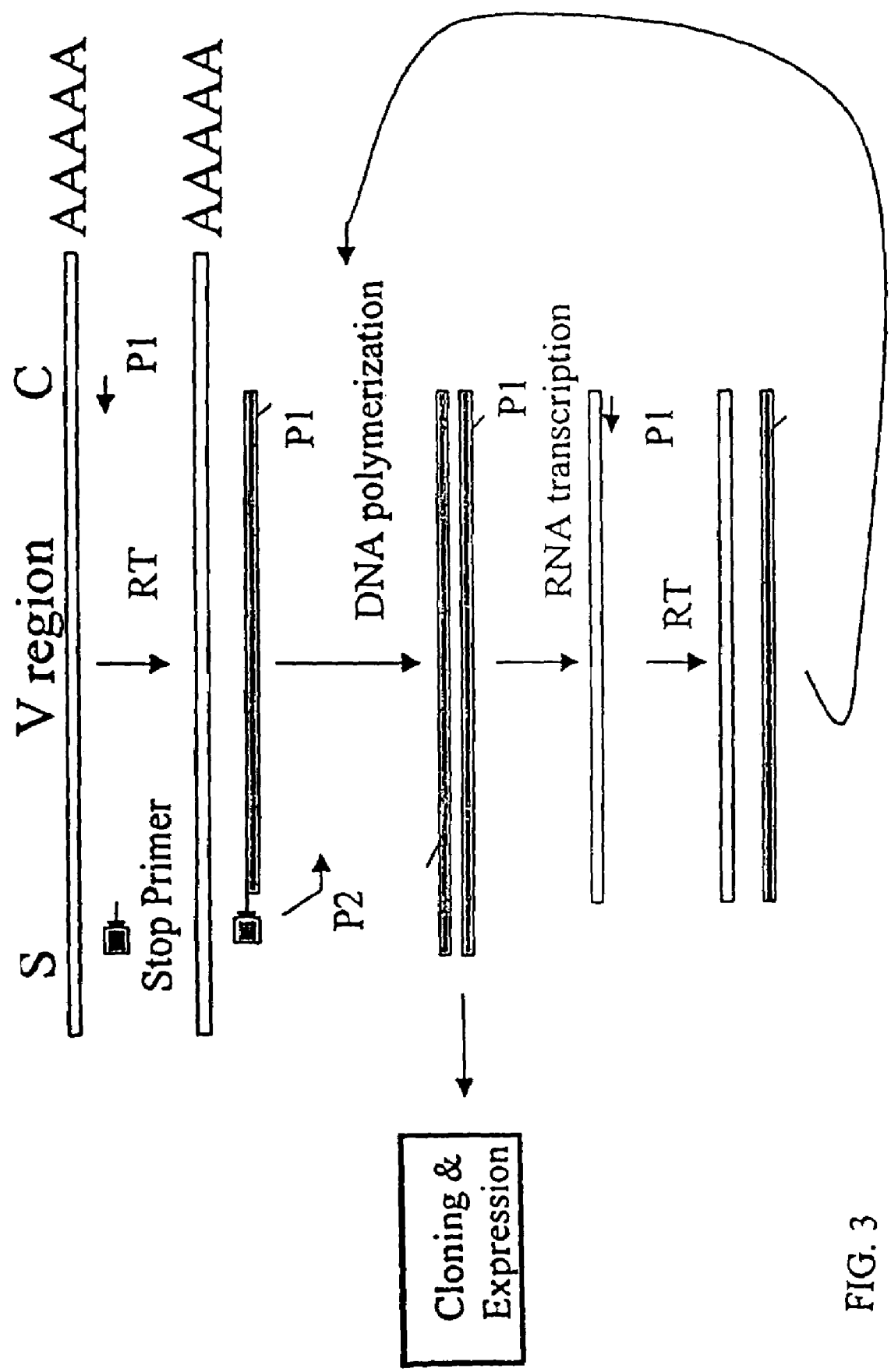
FIG. 3 illustrates a schematic diagram of another RNA transcription based amplification scheme for amplifying the immunoglobulin gene variable regions using mRNAs as the source, employing sense promoter-linked primers for RNA transcription and double stranding, and antisense primers for reverse transcription. A stop primer is used in the scheme to prevent over extension of the first strand cDNA beyond the sense primer site so that the ds RNA promoter template can be formed in the primer extension double stranding process.

In another embodiment, the $V_H$ and $V_L$ of the heavy and light chain gene repertoire are amplified into sense RNA transcripts. In one embodiment as depicted in FIG. 3, the antisense P1 primer is not linked with the RNA promoter sequence, rather, the sense P2 primer is linked with RNA promoter sequence. The mRNA transcripts are first reversed-transcribed into cDNAs by the antisense P1 primer in the presence of an antisense stop primer (the stop primer may or may not have a terminator at the 3'-end) and reverse transcriptase. The stop primer is situated immediately and adjacent to the 5'-terminus of the gene-specific portion of the sense P2 primer. The purpose of employing a stop primer is to prevent the first strand cDNA primed by the antisense P1 from over-extending beyond the P2 primer site so that ds cDNA can be made using the antisense P2 primer linked with the RNA promoter sequence (the promoter-linked primer) to generate ds RNA promoter sequences for RNA transcription. The ds cDNAs are made by the sense P2 primer extension on the first single-stranded (ss) cDNAs and ds RNA promoter template is made in the simultaneous extension of the first ss cDNAs with the RNA promoter oligonucleotide sequence in the sense P2 promoter-linked primer. The resulting ds cDNAs are transcribed into hundreds to thousands of copies of sense RNA transcripts. The sense RNA transcripts are amplified by antisense P1 reverse priming in a reverse transcription reaction and double-stranding by the sense P2 primer and RNA transcription of the ds DNA homologs, which can be further amplified by repeating the same process a few more times to generate the clonable $V_H$ and $V_L$ DNA homologs.

In another embodiment as depicted in FIG. 4, the antisense P1 primer is not linked with the RNA promoter sequence. The first strand cDNAs are synthesized by reverse priming of the mRNA by the antisense P1 primer. The 3'-end of the resultant cDNAs is modified with a poly $(G)_n$ tail by a terminal transferase (TdT). The sense P2 primer is a poly $(C)_nGG$ oligonucleotide linked with an RNA promoter sequence at the 5'-end. Double-stranded cDNAs are made by the sense P2 primer extension on the first strand cDNAs and the resulting ds cDNAs are used as the templates for the RNA polymerase to transcribe hundreds to thousands of copies of sense RNA transcripts. The sense RNA transcripts can be amplified further by firstly copied into cDNAs by reverse transcriptase from P1 primer and then tailed with poly $(G)_n$. The ss tailed cDNAs are primed with the sense P2 primer and converted into ds cDNA again as templates for RNA transcription amplification. This process can be repeated a couple of more times for sufficient amplification of the RNA transcripts of the $V_H$ and $V_L$ regions of the immunological heavy and light chain genes. The resulting RNA transcripts can be converted into ds DNAs by methods known in the art to produce the desired $V_H$ and $V_L$ DNA homologs for downstream cloning and expression purposes. The sense RNA transcripts contain the 5' terminal portions of the mRNA transcripts including, for example, ribosome binding sites and translation initiation sites.

Figure 5:
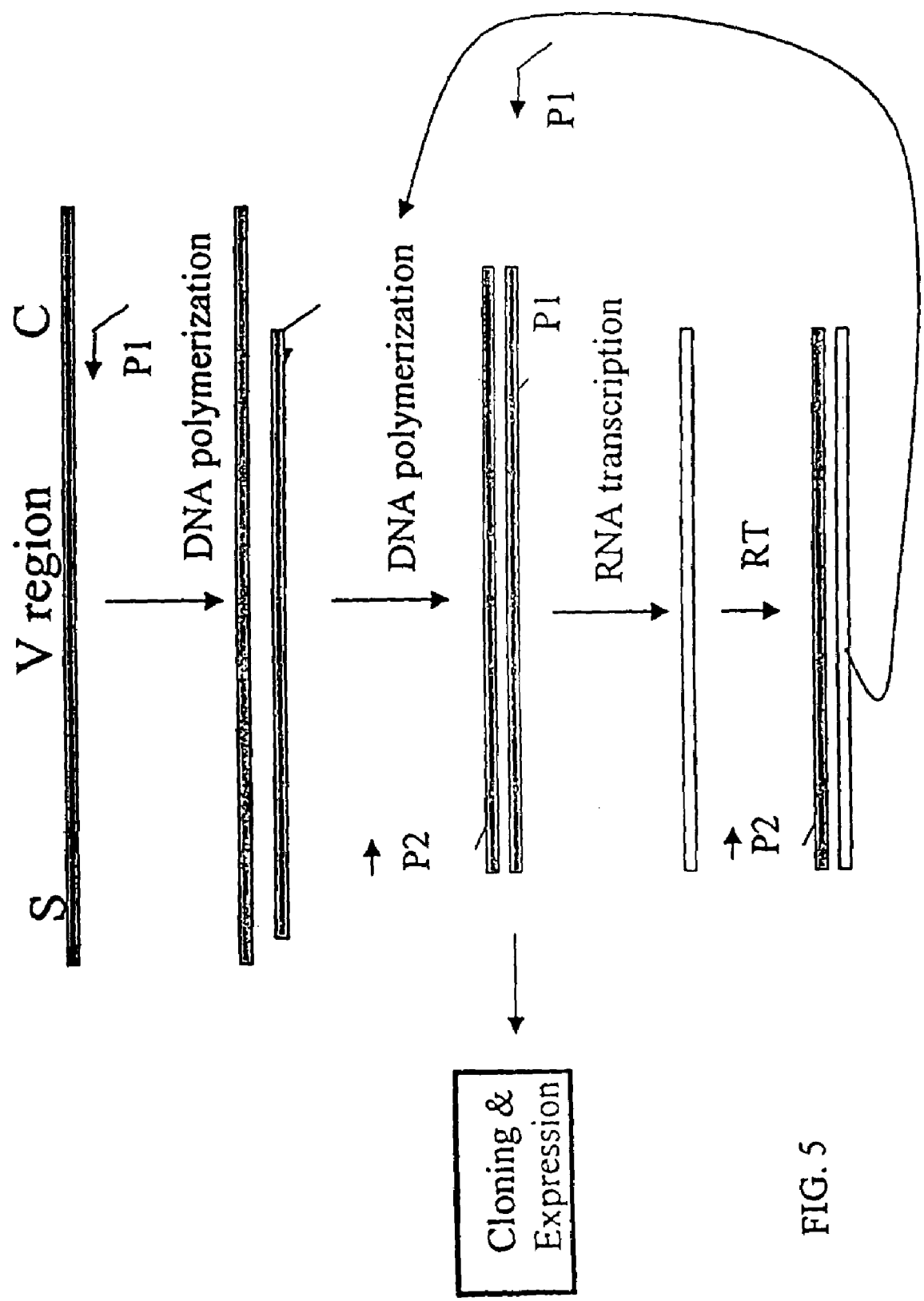
FIG. 5 illustrates a schematic diagram of another RNA transcription based amplification scheme for amplifying the immunoglobulin gene variable regions using genomic DNA as the source and employing antisense promoter-linked primers for RNA transcription.
Figure 6:
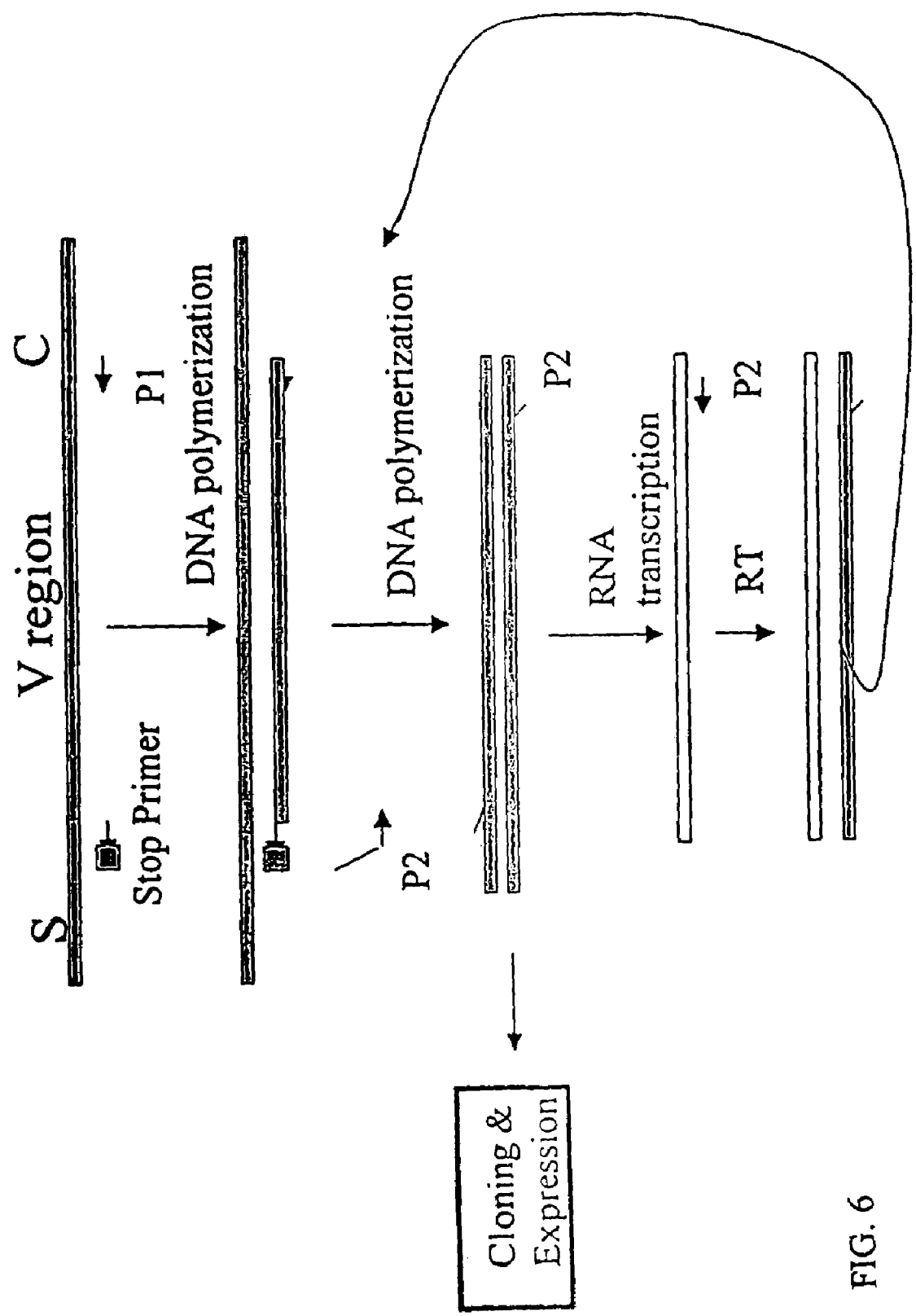
FIG. 6 illustrates a schematic diagram of another RNA transcription based amplification scheme for amplifying the immunoglobulin gene variable regions using genomic DNA as the source and employing sense promoter-linked primers for RNA transcription. A stop primer is used in the scheme to prevent over extension of the antisense DNA beyond the sense primer site so that the ds RNA promoter template can be formed in the primer extension double stranding process.

In another embodiment wherein the immunoglobulin repertoire sources are genomic DNAs from immunological tissues or cells, such as a hybridoma or stimulated immunological cells with rearranged immunoglobulin genes, the desired $V_H$ and $V_L$ DNA homologs are made, for example, as depicted in FIG. 5 or FIG. 6. The genomic DNAs are usually first denatured, typically by melting, into single strands. In one embodiment as depicted in FIG. 5, the antisense P1 primer is linked with the RNA promoter sequence and used to copy only once the sense DNA template into an antisense strand DNAs which are copied by the sense P2 primer into ds DNA containing the ds RNA promoter template at the P1 primer end for RNA transcription amplification. The amplified RNA transcripts are in the antisense orientation and are reverse transcribed into sense DNA by the sense P2 primer and reverse transcriptase. The sense-oriented ss DNAs are further copied into ds DNA by the antisense P1 primer and a DNA polymerase into the $V_H$ and $V_L$ DNA homologs, which can be further amplified by repeating the process. The sufficiently amplified $V_H$ and $V_L$ DNA homologs are clonable in the downstream cloning and expression exercise. In another embodiment as depicted in FIG. 6, the ds genomic DNAs are first copied once into antisense DNAs by the antisense P1 primer and a DNA-dependent DNA polymerase in the presence of a stop primer as described there before in FIG. 3. The copied antisense DNAs are further copied once by the RNA promoter-linked primer P2 into ds DNA and the ds RNA promoter template is made by the extension of the first antisense DNAs stopped by the stop primer at the adjacent site immediately 5' to the end of the P2 primer site. The ds copied DNAs are subject to an RNA transcription amplification to generate sense RNA transcripts, which can be reverse transcribed into ss cDNAs by the antisense P1 primer and a reverse transcriptase. The ss cDNAs then are double stranded by the sense P2 promoter-linked primer. The resulting ds DNAs can be further amplified by repeating the process to generate sufficient amounts of the $V_H$ and $V_L$ homologs.

The present invention also contemplates $V_H$ and $V_L$ DNA homolog production via co-amplification (using two pairs of primers), and multiplex amplification (using up to about 8, 9, 10 or more primer pairs of P1 and P2 type primers). As in the before discussed embodiments, a plurality of the P1 and P2 primers can be used in each transcription-based amplification, or an individual pair of P1 and P2 primers can be used. In any case, the amplification products of the transcription-based amplifications using the same or different combinations of P1 and P2 primers can be combined to increase the diversity of the gene library.

The DNA polymerization, reverse transcription and RNA transcription so discussed in the embodiments herein are performed using any suitable methods known in the art. Generally they occur in buffered aqueous solutions at preferred pH conditions with the P1 and/or P2 primers admixed with the buffers containing the template strand. A large molar excess of the P1 and/or P2 primers is advantageous or preferred to improve the efficiency of the processes involved.

The deoxyribonucleotide triphosphates dATP, dCTP, dGTP, and dTTP are admixed in the reverse transcription and the DNA polymerization reactions for making the DNA molecules. The ribonucleotide triphosphates ATP, CTP, GTP and TTP are also admixed in the DNA-Dependent RNA transcription reaction for making the RNA molecules.

Suitable enzymes for DNA-dependent DNA polymerization include, for example, *E. coli*, DNA polymerase I, Klenow fragment of *E. coli* DNA polymerase I, T4 DNA polymerase, other available DNA polymerases and other enzymes such as heat-stable enzymes such as Taq-like DNA polymerases, TTh-like DNA polymerase, C. therm polymerase, and combinations thereof. The suitable enzymes for the DNA-dependent RNA polymerization include RNA polymerases such as T3 RNA polymerase, T7 RNA polymerase, SP6 RNA polymerase, M13 RNA polymerase and viral replicase.

Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The $V_H$ and $V_L$ DNA homologs produced by the present transcription-based amplification are typically in double-stranded form and have contiguous or adjacent to each of their termini a nucleotide sequence defining an endonuclease restriction site. Digestion of the $V_H$ and $V_L$ DNA homologs having restriction sites at or near their termini with one or more appropriate endonucleases results in the production of homologs having cohesive termini of predetermined specificity for purpose of cloning into a vector or framework sequences.

The expression of the antigen-combining molecules of $V_H$ and $V_L$ genes can be achieved either via in vitro transcription and translation or by expression in a host cell through cloning into an expression vector known in the art. For in vitro transcription and translation expression of the immunological genes, the P1 and P2 primers are so designed to fuse appropriately into an antibody framework sequence or other scaffold sequences, which contains sequences necessary for adequate coupling of in vitro transcription and translation utilizing methods known in the art. The expression vectors can be selected to ensure expression in a wide range of suitable host cells or in selected host cells such as E. coli or mammalian cells. The $V_H$ and $V_L$ gene repertoire can be operatively fused with various surface proteins of a filamentous bacteriophage for displaying on the surface of the bacterial phage known in the art as phage display, see for example, Gao et al., supra.

The $V_H$ and $V_L$ DNA homologs can be separately cloned, expressed and combined into heterodimeric antibodies. Alternatively, the $V_H$ and $V_L$ genes can be operatively linked by a synthetic linker peptide to form a single chain $F_v$ or $scF_v$ as known in the art. Both heterodimeric antibodies including the $F_{ab}$ antibodies and the $scF_v$ antibodies can be displayed by phage display systems or generated in an in vitro translation system known in the art.

In preferred embodiments, the transcription-based amplification process of the present invention is used not only to amplify the $V_H$ and/or $V_L$ DNA homologs of the immunological gene repertoire, but also to induce mutations within the library and thereby provide a library having a greater heterogeneity. Mutations can be deliberately introduced in the $V_H$ and $V_L$ DNA homologs by certain error-prone thermostable DNA-dependent DNA polymerases such as Taq-like polymerases known in the art. In other cases, mutations can be induced during the DNA polymerization or reverse transcription reactions by incorporating into the reaction admixture nucleotide derivatives such as inosine, xanthine, hypoxanthine, and other labeled nucleotides, not normally found in the nucleic acids of the repertoire being amplified. During subsequent in vivo or in vitro amplification reactions, the nucleotide derivatives will be replaced with substitute nucleotides thereby inducing point mutations in the $V_H$ and $V_L$ DNA homolog repertoire.

While the above discussion relates to the cloning of DNA sequences, as known in the art, RNA's can be cloned also. Thus, the transcribed single stranded RNA molecules, for example, particularly those produced, when two primers are used, with the polymerase promoter on the second of the two primers.

4a. In vivo expression of the $V_H$ and $V_L$ polypeptides in an appropriate host, including prokaryotic and eukaryotic hosts, either separately or in the same cell, either on the same or different expression vectors, and either in linked single chain ($scF_v$) form or separate heterodimeric receptor form. Alternatively, the $V_H$ and/or $V_L$ DNA homolog repertoire produced by the present invention have by design restriction enzyme sites for cloning into a vector for amplification and/or expression in a host cell.

The various vectors suitable for replicating and expressing the $V_H$ and/or $V_L$ gene repertoire are available from many commercial vendors and are well known in the art. Those vectors include a prokaryotic expression vector such as plasmid vector containing a prokaryotic promoter capable of directing the expression (transcription and translation) of the $V_H$ and/or $V_L$ DNA homologs in a bacterial host cell, such as *E. coli* transformed therewith. Typical of such plasmid vectors are pUC8, pUC9, pBR322, pBR329, pPL, pKK223 and other vectors known in the art and available from commercial vendors such as BioRad Laboratories (Richmond, Calif.), Amersham Biosciences (Piscataway, N.J.), Invitrogen (Carlsbad, Calif.) and Stratagene (La Jolla, Calif.). Those expression vectors also include eukaryotic expression vectors for expressing polypeptides in eukaryotic cells such as yeast and mammalian cells. Many eukaryotic expression vectors, such as pSVL, pCDNAneo, etc., are well known in the art and are available from several commercial sources. As well known in the art, both prokaryotic and eukaryotic expression vectors contain selectable drug resistant drug markers such as ampicillin or tetracycline resistant gene markers for prokaryotic vectors and neomycin selection marker for eukaryotic expression vectors. In preferred embodiments, the expression of the $V_H$ and/or $V_L$ gene repertoire in mammalian cells are carried out by using retroviral expression vectors, which vector sequences including the promoter sequences are derived from the long terminal repeat (LTR) region of a retrovirus genome. There are many retroviral expression vectors are available from commercial vendors such as Stratagene (La Jolla, Calif.) and Invitrogen (Carlsbad, Calif.) and are well known in the art.

In preferred embodiments, diverse heterodimeric antibodies are expressed from randomly combining of the $V_H$ and $V_L$ DNA homologs of the diverse libraries in vitro for polycistronic expression from individual vectors. A library of vectors is generated with each vector capable of expressing, under the control of a single promoter, one $V_H$ DNA homolog and one $V_L$ DNA homolog, with these $V_H$ and $V_L$ DNA homologs being randomly combined to produce the heterodimeric antibody in a single host cell.

The heterodimeric antibody of one $V_H$ and one $V_L$ combination can also be produced from two distinctive expression vectors with two different drug resistant selection markers. A cell selectively surviving two drugs contains at least one $V_H$ and at least one $V_L$ to form a randomly combined heterodimeric antibody. In one preferred embodiment, the linear double stranded lambda vectors such as Lambda Zap or its derivative vectors from Stratagene (La Jolla, Calif.) are used and are well known in the art.

As well known in the art, each of the vectors discussed in the present invention may comprise a ribosome binding site, a leader sequence, a polylinker sequence for restriction enzyme sites, a stop codon, a selectable marker, or a peptide tag in certain cases.

The generation of the diverse heterodimeric antibodies or the random combination of the $V_H$ and $V_L$ is accomplished by ligating $V_H$ DNA homologs into a first vector, typically at a restriction site or sites within the polylinker sequence of the vector. Similarly, $V_L$ DNA homologs are ligated into a second vector, thereby creating two diverse populations of expression vectors. It does not matter which type of DNA homolog, i.e., $V_H$ or $V_L$, is ligated to which vector, but it is preferred to have all $V_H$ DNA homologs ligated to either the first or second vector and all $V_L$ DNA homologs ligated to the other of the first or second vector. The members of both populations are then cleaved with an endonuclease at the shared restriction site, typically by digesting both populations with the same enzyme. The resulting product is two diverse populations of restriction fragments where the members of one have cohesive termini complementary to the cohesive termini of the members of the other. The restriction fragments of the two populations are randomly ligated to one another, i.e., a random, interpopulation ligation is performed, to produce a diverse population of vectors each having a $V_H$ and $V_L$ DNA homolog located in the same reading frame and under the control of the promoter of the second vector. Subsequent recombinations can be achieved through cleavage at the shared restriction site, which is typically reformed on ligation of members from the two populations, followed by subsequent religations. The diverse heterodimeric antibodies or the $F_v$ antibodies of randomly combined $V_H$ and $V_L$ are produced in host cells by transforming the host cells with the before-described recombined $V_H$ and $V_L$ gene repertoire.

The host cell for replicating the vectors and expressing the $V_H$ and/or $V_L$ gene repertoire can be either prokaryotic or eukaryotic. Bacterial cells are preferred prokaryotic host cells and typically are a strain of $E.$ $coli$ such as, for example, the E. coli strain DH5 available from Invitrogen (Carlsbad, Calif.). Preferred eukaryotic host cells include yeast and mammalian cells, preferably vertebrate cells such as those from a mouse, rat, monkey or human cell line.

Transformation of appropriate cell hosts with a recombinant DNA molecule of the present invention is carried out by such methods as electroporation, lipofection, and other transfection agents known in the art and available from many vendors, see, for example, Maniatis et al., Molecular Cloning, a Laboratory Manual, Cold Spring Harbor Laboratory, Cold Spring Harbor, N.Y. (1982).

4b. In vitro expression of the $V_H$ and $V_L$ polypeptides in an in vitro transcription and/or translation system, either on the same or different frameworks, and either in linked single chain (scF$_v$) form or separate heterodimeric receptor form can be practiced using materials and methods known in the art, such as the PROfusion system described in U.S. Pat. No. 6,214,553 to Szostak, et al. In general, the PROfusion technology consists of an in vitro or in situ transcription/translation protocol that generates protein covalently linked to the 3' end of the very mRNA, i.e., an RNA-protein fusion. This is accomplished by synthesis and in vitro or in situ translation of an mRNA molecule with a peptide acceptor attached to the 3' end of the message. One preferred peptide acceptor is puromycin, a nucleoside analog that adds to the C-terminus of a growing peptide chain and terminates translation. In one preferred design, a DNA sequence is included between the end of the message and the peptide acceptor which is designed to cause the ribosome to pause at the end of the open reading frame, providing additional time for the peptide acceptor (for example, puromycin) to accept the nascent peptide chain before hydrolysis of the peptidyl-tRNA linkage. Typically, the mRNA-protein fusion system comprises an in vitro expression unit comprising a untranslated region containing an RNA polymerase binding sequence, a ribosome binding sequence, and a translation initiation signal. The in vitro transcription and translation unit is to fuse with the desired polynucleotide sequence tagged with stop codon and possibly the poly-A site for expressing fused the polypeptide in frame.

In a preferred embodiment employing such in vitro transcription and translation systems to express the $V_H$ and/or $V_L$ gene repertoire, the $V_H$ DNA homologs are fused to the 3'-end of the first in vitro transcription and translation unit capable of expressing one $V_H$ DNA homolog and likewise, the $V_L$ DNA homologs are fused into a second transcription and translation unit. The first and second transcription and translation units are subjected to in vitro transcription and translation in the PROfusion system to produce the $V_H$ and $V_L$ gene repertoire, separately. The separately expressed $V_H$ and $V_L$ are mixed to form randomly combined heterodimeric $F_v$ antibodies in vitro.

In another preferred embodiment, the $V_H$ and $V_L$ DNA homologs are fused with a linker oligonucleotide coding for a linker peptide such as GlyGlyGlyGlySer (Gly$_4$Ser)(SEQ ID NO:1). The single chain polypeptide of $V_H$-(GlyGlyGlyGlySer(SEQ ID NO:1))$_n$-V$_L$ or $V_L$-GlyGlyGlyGlySer(SEQ ID NO:1))$_n$-V$_H$ are fused in frame of the transcription and translation unit for in vitro transcription and translation in the PROfusion system to produce $scF_v$ antibodies or $scF_v$ antibody library.

The heterodimeric antibodies or the $scF_v$ antibodies can also be made employing the ribosome display technology as described in the PCT patent application WO 09105058A1 by Glenn Kawasaki. Ribosome display is a method for producing polypeptides, comprising: (a) constructing an in vitro expression unit comprising an untranslated region containing an RNA polymerase binding sequence, a ribosome binding sequence, and a translation initiation signal, said expression unit being capable of producing mRNA; (b) attaching one or more semi-random nucleotide sequences to said expression unit; (c) transcribing or replicating the sequences associated with the expression-unit and semi-random nucleotide sequences to produce RNA; (d) translating said RNA to produce polysomes under conditions sufficient to maintain said polysomes; (e) binding said polysomes to a substance of interest; (f) isolating said polysomes that bind to said substance of interest; (g) disrupting said isolated polysomes to release mRNA; (h) recovering said mRNA; (i) constructing cDNA from said recovered mRNA; and (j) expressing said cDNA to produce novel polypeptides.

Similar to the embodiments employing the PROfusion method, the heterodimeric or $scF_v$ antibody libraries can be produced by fusing the $V_H$ or $V_L$ or the $V_H$-(GlyGlyGlyGlySer (SEQ ID NO:1))$_n$-$V_L$ or the $V_L$-(GlyGlyGlyGlySer(SEQ ID NO:1))$_n$-$V_H$ molecules with the in vitro transcription/translation unit sequence.

5. The antibody libraries produced by the present invention can be screened for preselected antigen binding or catalytic activities. In the case of using antibody libraries expressed in a host cell, the preferred screening assays are those where the binding of ligand by the receptor produces a detectable signal, either directly or indirectly. Such signals include, for example, the production of a complex, formation of a catalytic reaction product, the release or uptake of energy, and the like. In preferred embodiments, the immunological methods as well known in the art are employed, especially to perform immunochemical assays against a preselected epitope or a ligand.

6. The present invention contemplates an antibody gene library, preferably produced by a transcription-based amplification method as described herein, containing at least about $10^3$, preferably at least about $10^5$, more preferably at least about $10^7$, more preferably at least about $10^8$ and most preferably at least $10^9$ different $V_H$ and/or $V_L$ DNA homologs.

In preferred embodiments, a substantial portion of the $V_H$ and/or $V_L$ DNA homologs present in the antibody library are operatively linked in a vector, preferably operatively linked for expression by an expression vector or operatively fused with an in vitro transcription/translation unit.

The present invention contemplates a host cell or cells transformed therewith an antibody library containing the $V_H$ and/or $V_L$ DNA homologs. The present invention also contemplates a medium suitable for in vitro transcription/translation therewithin having the $V_H$ and/or $V_L$ DNA homologs fused with the in vitro transcription/translation unit. The medium comprises water, buffering salts and the like and the transcription/translation unit fused with the $V_H$ and/or $V_L$ DNA homologs.

The libraries of the instant invention are well represented with clones from a wide range of molecules. The instant methods enable capture of genes previously poorly amplified or cloned, or not cloned at all. Moreover, by modifying the captured genes, for example, when a DNA or an RNA, the diversity of the library can be enhanced beyond what represents the naturally occurring repertoire. For example, a generalized mutagenesis or site-directed mutagenesis can be conducted on the nucleic acids to promote diversity of the members of the library.

The antibodies and antigen-binding fragments and constructs thereof, are human antibodies. Thus, the risk of generating a "serum sickness" reaction to xenogenic, non-human epitopes is minimized. The antibodies can find use in any of the art-recognized uses for antibody and antibody-type molecules. For example, an antibody obtained from an instant library can be used as an affinity reagent to purify antigen from a mixture. An antibody of the instant invention can be used in an assay, whether in vitro or in vivo. The antibody can be used in direct or indirect assays, can be labeled and so on as known in the art. Thus, an antibody of interest can be used in known diagnostic assays, such as fluorescence assays, ELISA's, RIA's and the like. As indicted, as a human antibody, the instant antibody is less antigenic and can be used as, for example, an imaging agent along with an appropriate detecting device, such as a fluoroscope or a gamma camera. An instant antibody also can find use as a therapeutic agent. For example, the antibody can be effective alone in disrupting a pathogen or pathogenic state in a human. Also, the antibody can be conjugated to a cytotoxic agent, such as a radionuclide, a poison, such as ricin, and so on. Thus, the antibody serves as a targeting agent. There are many uses of antibodies, as known in the art, and any one of those uses is contemplated to be practicable using an antibody obtained by the methods and from the libraries of interest. The various methods of using an antibody are well known to the artisan, and such use is a design choice. Any of a number of treatises can be consulted regarding the uses of antibody, and particularly human antibody.

The invention now will be exemplified further in the following non-limiting examples.

EXAMPLES

Example 1

Gene-Specific Oligonucleotide and RNA Promoter-Linked Primer Selection

The nucleotide sequences coding for the human immunoglobulin complimentary determining region (CDR) are highly variable (Marks, J. D. et al., *J. Mol. Biol.*, 222: 581-597(1991); Haidaris, C. G. et al., 257:185-202 (2001); Welschof, M. et al., *J. Immunol. Methods*, 179:203-214 (1995); Marks, J. D. et al., *Eur. J. Immunol.*, 21:985-991 (1991); and Haard, H. J. D. et al., *J. Biol. Chem.*, 274:18218-18230(1999)). However, there are several regions of conserved sequences that flank the human $V_H$ domains, containing substantially conserved nucleotide sequences, i.e., sequences that will hybridize to the same primer sequence in a number of different genes. Therefore, gene-specific oligonucleotide primers can be selected for both gene-specific primers and the promoter-linked primers and synthesized to hybridize to the conserved sequences for reverse transcription, double stranding and RNA transcription reactions as described in the present invention. For transcriptional amplification of the human $V_H$ domains, the $V_H$-specific oligonucleotide primer sequences are either in the sense orientation or antisense orientation. In all cases, the sense primers (Table 1) were chosen to be either in the conserved N-terminus region of the human $V_H$ domains and to be homologous to the sense mRNA transcripts or complementary to the first strand cDNAs or at the 5' terminus, and the antisense primers were chosen to be in the flanking J region and to be complementary to the sense mRNA transcripts. To reduce the number of oligonucleotide primers to be synthesized, certain wobble nucleotides were incorporated into the gene-specific primer sequences. As known well in the art, the standard code letters for specifying a wobble are: R=A/G, Y=C/T, M=A/C, K=G/T, S=C/G, W=A/T, B=C/G/T, D=A/G/T, H=A/C/T, V=A/C/G, and N=A/C/G/T. To amplify the $V_H$ domains by producing the antisense RNA transcripts intermediates as discussed in FIG. 1 and FIG. 2, the T7 RNA promoter sequence (T7:5'-dCCA GTG AAT TGT AAT ACG ACT CAC TAT AGG GAA-3' (SEQ ID NO:2)) is linked to the 5' end of the antisense primers. Alternatively, the T7 RNA promoter sequence is linked to 5' end of the sense primers to produce the sense RNA transcripts intermediates as presented in FIG. 3 and FIG. 4.

Additionally, $V_H$-specific amplification includes unique antisense primers that were designed to be complementary to a portion of the first constant region domain of the $\gamma_1$ heavy chain mRNA. These primers will produce $V_H$ DNA homologs containing polynucleotides coding for amino acids from the $V_H$ and the first constant region domains of the heavy chain. These DNA homologs can therefore be used to produce $F_{ab}$ fragments rather than an $F_v$. The primers may contain restriction sites, stop codons, peptide linkers and the like, as disclosed herein. Restriction sites, stop codons and sequences encoding linkers are underlined.

TABLE 1

Human $V_H$-Specific Primers

Antisense EcoRI & Stop Codon-Linked $HJ_H$ Primers:
```
aHJ_H-1: 5'-dTGG AAT GAA TTC GAT TGC TAG TCA GAC GGT GAC CAG
              GGT GCC-3' (SEQ ID NO:3)

aHJ_H-2: 5'-dTGG AAT GAA TTC GAT TGC TAG TCA GAC GGT GAC CAT
              TGT CCC-3' (SEQ ID NO:4)

aHJ_H-3: 5'-dTGG AAT GAA TTC GAT TGC TAG TCA GAC GGT GAC CAG
              GGT TCC-3' (SEQ ID NO:5)

aHJ_H-4: 5'-dTGG AAT GAA TTC GAT TGC TAG TCA GAC GGT GAC CGT
              GGT CCC-3' (SEQ ID NO:6)
```

Sense T7 & Not I-Linked Primer:
```
      5'-dCCA GTG AAT TGT AAT ACG ACT CAC TAT AGG GAA CGG CAT
         GGA ATG CGG CCG CCC CCC CCC C-3' (SEQ ID NO:7)
```

T7 & Peptide Linker(PL)-Linked Antisense $HJ_H$ Primers:
```
aT7PLHJ_H-1: 5'-dCCA GTG AAT TGT AAT ACG ACT CAC TAT AGG GAA
                 AGA GCC GCC GCC GCC TGA GGA GAC GGT GAC CAG
                 GGT GCC-3' (SEQ ID NO:8)

aT7PLHJ_H-2: 5'-dCCA GTG AAT TGT AAT ACG ACT CAC TAT AGG GAA
                 AGA GCC GCC GCC GCC TGA GGA GAC GGT GAC CAT
                 TGT CCC-3' (SEQ ID NO:9)

aT7PLHJ_H-3: 5'-dCCA GTG AAT TGT AAT ACG ACT CAC TAT AGG GAA
                 AGA GCC GCC GCC GCC TGA GGA GAC GGT GAC CAG
                 GGT TCC-3' (SEQ ID NO:10)

aT7PLHJ_H-4: 5'-dCCA GTG AAT TGT AAT ACG ACT CAC TAT AGG GAA
                 AGA GCC GCC GCC GCC TGA GGA GAC GGT GAC CGT
                 GGT CCC-3' (SEQ ID NO:11)
```

Sense $HV_H$ Primers:
```
sHV_H-1: 5'-CAG CCG GCC ATG GCA CAG GTN CAG CTG GTR CAG TCT GG-3'   (SEQ ID NO:12)

sHV_H-2: 5'-CAG CCG GCC ATG GCA CAG GTC CAG CTG GTR CAG TCT GGG G-3' (SEQ ID NO:13)

sHV_H-3: 5'-CAG CCG GCC ATG GCA CAG GTK CAG CTG GTG SAG TGT GGG-3'   (SEQ ID NO:14)

sHV_H-4: 5'-CAG CCG GCC ATG GCA CAG GTC ACC TTG ARG GAG TCT GGT CC-3' (SEQ ID NO:15)

sHV_H-5: 5'-CAG CCG GCC ATG GCA CAG GTG CAG CTG GTG GAG WCT GG-3'   (SEQ ID NO:16)

sHV_H-6: 5'-CAG CCG GCC ATG GCA CAG GTG CAG CTG GTG SAG TCY GG-3'   (SEQ ID NO:17)

sHV_H-7: 5'-CAG CCG GCC ATG GCA CAG GTG CAG CTG CAG GAG TCG G-3'    (SEQ ID NO:18)

sHV_H-8: 5'-CAG CCG GCC ATG GCA CAG GTG CAG CTG TTG SAG TCT G-3'    (SEQ ID NO:19)
```

TABLE 1-continued

Human V$_H$-Specific Primers

| | |
|---|---|
| sHV$_H$-9: 5'-CAG CCG GCC ATG GCA CAG GTG CAG CTG GTG CAA TCT G-3' | (SEQ ID NO:20) |
| sHV$_H$-10: 5'-CAG CCG GCC ATG GCA CAG GTG CAG CTG CAG GAG TCC GG-3' | (SEQ ID NO:21) |
| sHV$_H$-11: 5'-CAG CCG GCC ATG GCA CAG GTG CAG CTA CAG CAG TGG G-3' | (SEQ ID NO:22) |
| sHV$_H$-12: 5'-CAG CCG GCC ATG GCA CAG GTA CAG CTG CAG CAG TCA G-3' | (SEQ ID NO:23) |

The nucleotide sequences coding for the human V$_L$ (both the V$_K$ and V$_\lambda$ isotypes) CDRs are also highly variable. However, there are several regions of conserved sequences that flank the V$_L$ CDR domains including the J$_L$, V$_L$ framework regions and V$_L$ leader/promoter. Therefore, VL-specific primers that hybridize to the conserved sequences are selected and synthesized in the similar fashion as for the human V$_H$ domains as discussed herebefore.

Table 2 lists the human V$_K$-specific primers and Table 3 lists human V$_\lambda$-specific primers used for the present invention.

TABLE 2

Human V$_K$-Specific Primers

Antisense XhoI & Stop Codon-Linked HJ$_k$ Primers:

| | |
|---|---|
| aHJ$_K$-1: 5'-dTGG AAT TCT CGA GAT TGC TAG TCA ACG TTT GAT TTC CAC CTT GGT CCC-3' | (SEQ ID NO:24) |
| aHJ$_K$-2: 5'-dTGG AAT TCT CGA GAT TGC TAG TCA ACT TTT GAT CTC CAG CTT GGT CCC-3' | (SEQ ID NO:25) |
| aHJ$_K$-3: 5'-dTGG AAT TCT CGA GAT TGC TAG TCA ACG TTT GAT ATC CAC TTT GGT CCC-3' | (SEQ ID NO:26) |
| aHJ$_K$-4: 5'-dTGG AAT TCT CGA GAT TGC TAG TCA ACG TTT GAT CTC CAC CTT GGT CCC-3' | (SEQ ID NO:27) |
| aHJ$_K$-5: 5'-dTGG AAT TCT CGA GAT TGC TAG TCA ACG TTT AAT CTC CAG TCG TGT CCC-3' | (SEQ ID NO:28) |

Sense T7 & EcoRI-linked Primer:

| | |
|---|---|
| 5'-dCCA GTG AAT TGT AAT ACG ACT CAC TAT AGG GAA CGG CAT GGA ATG AAT TCC CCC CC-3' | (SEQ ID NO:29) |

T7-Linked Antisense HJk Primers:

| | |
|---|---|
| aT7HJ$_K$-1: 5'-dCCA GTG AAT TGT AAT ACG ACT CAC TAT AGG GAA TGG AAT TCG GCC CCG AGG CCA CGT TTG ATT TCA CCT TGG TCC C-3' | (SEQ ID NO:30) |
| aT7HJ$_K$-2: 5'-dCCA GTG AAT TGT AAT ACG ACT CAC TAT AGG GAA TGG AAT TCG GCC CCG AGG CCA CGT TTG ATC TCA GCT TGG TCC C-3' | (SEQ ID NO:31) |
| aT7HJ$_K$-3: 5'-dCCA GTG AAT TGT AAT ACG ACT CAC TAT AGG GAA TGG AAT TCG GCC CCG AGG CCA CGT TTG ATA TCC ACT TTG GTC CC-3' | (SEQ ID NO:32) |
| aT7HJ$_K$-4: 5'-dCCA GTG AAT TGT AAT ACG ACT CAC TAT AGG GAA TGG AAT TCG GCC CCG AGG CCA CGT TTG ATC TCC ACC TTG GTC CC-3' | (SEQ ID NO:33) |
| aT7HJ$_K$-5: 5'-dCCA GTG AAT TGT AAT ACG ACT CAC TAT AGG GAA TGG AAT TCG GCC CCG AGG CCA CGT TTA ATC TCC AGT CGT GTC CC-3' | (SEQ ID NO:34) |

TABLE 2-continued

| Human V$_K$-Specific Primers |

Sense Peptide Linker-Linked HV$_K$-Specific Primers:

sPLHV$_K$-1: 5'-TCC TCA GGC GGC GGC TCT GGC GGA GGT GGC AGC  (SEQ ID NO:35)
GGC GGT GGC GGA TCC GAC ATC CAG ATG ACC CAG TCT CC-3' sPLHV$_K$-2: 5'-TCC TCA GGC GGC GGC TCT GGC GGA GGT GGC AGC  (SEQ ID NO:36)
GGC GGT GGC GGA TCC GAT GTT GTG ATG ACT CAG TCT CC-3' sPLHV$_K$-3: 5'-TCC TCA GGC GGC GGC TCT GGC GGA GGT GGC AGC  (SEQ ID NO:37)
GGC GGT GGC GGA TCC GAA ATT GTG TTG ACG CAG TCT CC-3' sPLHV$_K$-4: 5'-TCC TCA GGC GGC GGC TCT GGC GGA GGT GGC AGC  (SEQ ID NO:38)
GGC GGT GGC GGA TCC GAC ATC GTG ATG ACC CAG TCT CC-3' sPLHV$_K$-5: 5'-TCC TCA GGC GGC GGC TCT GGC GGA GGT GGC AGC  (SEQ ID NO:39)
GGC GGT GGC GGA TCC GAA ACG ACA CTC ACG CAG TCT CC-3' sPLHV$_K$-6: 5'-TCC TCA GGC GGC GGC TCT GGC GGA GGT GGC AGC  (SEQ ID NO:40)
GGC GGT GGC GGA TCC GAA ATT GTG CTG ACT CAG TCT CC-3'

TABLE 3

| Human V$_\lambda$-Specific Primers |

Antisense XhoI & Stop Codon-Linked HJ$_\lambda$Primers:

aHJ$_\lambda$-1: 5'-dTGG AAT TCT CGA GAT TGC TAG TCA ACC TAG GAC GGT  (SEQ ID NO:_)
GAC CTT GGT CCC-3' (SEQ ID NO:41)

aHJ$_\lambda$-2: 5'-dTGG AAT TCT CGA GAT TGC TAG TCA ACC TAG GAC GGT  (SEQ ID NO:_)
CAG CTT GGT CCC-3' (SEQ ID NO:42)

aHJ$_\lambda$-3: 5'-dTGG AAT TCT CGA GAT TGC TAG TCA ACC TAA AAC GGT  (SEQ ID NO:_)
GAG CTG GGT CCC-3' (SEQ ID NO:43)

Sense T7 & EcoRI-linked Primer:

5'-dCCA GTG AAT TGT AAT ACG ACT CAC TAT AGG GAA CGG  (SEQ ID NO:_).
CAT GGA ATG AAT TCC CCC CCC CC-3' (SEQ ID NO:44)

T7-Linked Antisense HJ$_\lambda$Primers:

aT7HJ$_\lambda$-1: 5'-dCCA GTG AAT TGT AAT ACG ACT CAC TAT AGG GAA TGG  (SEQ ID NO:_)
AAT TCG GCC CCG AGG CCA CCT AGG ACG GTG ACC TTG GGT CCC-3' (SEQ ID NO:45)

aT7HJ$_\lambda$-2: 5'-dCCA GTG AAT TGT AAT ACG ACT CAC TAT AGG GAA TGG  (SEQ ID NO:_)
AAT TCG GCC CCG AGG CCA CCT AGG ACG GTC AGC TTG GGT CCC-3' (SEQ ID NO:46)

aT7HJ$_\lambda$-3: (SEQ ID NO:_)
5'-dCCA GTG AAT TGT AAT ACG ACT CAC TAT AGG GAA TGG
AAT TCG GCC CCG AGG CCA CCT AAA AACG GTG AGC TG
GGT CCC-3' (SEQ ID NO:47)

Sense Peptide Linker-Linked HV$_\lambda$Specific Primers:

sPLHV$_\lambda$-1: 5'-TCC TCA GGC GGC GGC TCT GGC GGA GGT GGC AGC  (SEQ ID NO:_)
GGC GGT GGC GGA TCC CAG TCT GTG TTG ACG CAG CCG CC-3' (SEQ ID NO:48)

TABLE 3-continued

Human V$_\lambda$-Specific Primers sPLHV$_\lambda$-2: 5'-TCC TCA GGC GGC GGC GGC TCT GGC GGA GGT GGC AGC    (SEQ ID NO:_)
        GGC GGT GGC GGA TCC CAG TCT GCC CTG ACT CAG CCT
        GC-3' (SEQ ID NO:49)

sPLHV$_\lambda$-3: 5'-TCC TCA GGC GGC GGC GGC TCT GGC GGA GGT GGC AGC    (SEQ ID NO:_)
        GGC GGT GGC GGA TCC TCC TAT GTG CTG ACT CAG CCA
        CC-3' (SEQ ID NO:50)

sPLHV$_\lambda$-4: 5'-TCC TCA GGC GGC GGC GGC TCT GGC GGA GGT GGC AGC    (SEQ ID NO:_)
        GGC GGT GGC GGA TCC TCT TCT GAG CTG ACT CAG GAC
        CC-3' (SEQ ID NO:51)

sPLHV$_\lambda$-5: 5'-TCC TCA GGC GGC GGC GGC TCT GGC GGA GGT GGC AGC    (SEQ ID NO:_)
        GGC GGT GGC GGA TCC CAC GTT ATA CTG ACT CAA CCG
        CC-3' (SEQ ID NO:52)

sPLHV$_\lambda$-6: 5'-TCC TCA GGC GGC GGC GGC TCT GGC GGA GGT GGC AGC    (SEQ ID NO:_)
        GGC GGT GGC GGA TCC CAG GCT GTG CTC ACT CAG CCG
        TC-3' (SEQ ID NO:53)

sPLHV$_\lambda$-7: 5'-TCC TCA GGC GGC GGC GGC TCT GGC GGA GGT GGC AGC    (SEQ ID NO:_)
        GGC GGT GGC GGA TCC AAT TTT ATG CTG ACT CAG CCC
        CA-3' (SEQ ID NO:54)

Table 4 lists oligonucleotides that can be used for fusing variable DNA homologs to form a single chain antibody as discussed in Example 10.

TABLE 4

Human scF$_v$ Primers

Sense Sfi scF$_v$ Primer:
5'-TTG TTA TTA CTC GCG GCC CAG CCG GCC ATG GCA CAG GT-3')   (SEQ ID NO:55)

Antisense Sfi scF$_v$ Primer:
5'-GTC CTC GTC GAC TGG AAT TCG CCC CGA GCC AC-3')    (SEQ ID NO:56)

Additional antisense primers can be designed and synthesized to hybridize to the constant region of either kappa or lambda mRNA to produce the $V_K$ or $V_\lambda$ DNA homologs coding for constant region amino acids of either kappa or lambda chain to produce an $F_{ab}$ fragment rather than an $F_v$.

All primers and oligonucleotides used herein and shown on Tables 1-3 are obtainable commercial customer oligonucleotide synthesis companies such as Invitrogen (Carlsbad, Calif.) or are synthesized on an Applied Biosystems DNA synthesizer, model 381A, using the instructions and recommendations of the manufacturer.

Example 2

Preparation of Source mRNAs Containing the $V_H$ and $V_L$ Gene Repertoire

Total cellular RNA was prepared from the blood cells collected from a pool of patients using the RNA preparation methods well known in the art as described by Chomczynski et al., Anal Biochem., 162:156-159 (1987) and the RNA isolation kit produced by QIAGEN GmbH (Hilden, Germany).

Messenger RNA (mRNA) enriched for sequences containing long poly A tracts was prepared from the total cellular RNA using methods described in "Molecular Cloning: A Laboratory Manual", Maniatis et al., eds., Cold Spring Harbor Laboratory, New York, (1982). Briefly, the total RNA isolated from the blood cells prepared as described above was resuspended in 1 ml of DEPC-H$_2$O and maintained at 65° C. for 5 minutes. One ml of 2×high salt loading buffer consisting of 100 mM Tris-HCl, 1 M sodium chloride, 2.0 mM disodium ethylenediamine tetraacetic acid (EDTA) at pH 7.5, and 0.2% sodium dodecyl sulfate (SDS) was added to the resuspended RNA and the mixture allowed to cool to room temperature. The mixture was then applied to an oligo-dT (Collaborative Research Type 2 or Type 3) column that was previously prepared by washing the oligo-dT with a solution containing 0.1 M sodium hydroxide and 5 mM EDTA and then equilibrating the column with DEPC-H$_2$O. The eluate was collected in a sterile polypropylene tube and reapplied to the same column after heating the eluate for 5 minutes at 65° C. The oligo-dT column was then washed with 2 ml of high salt loading buffer consisting of 50 mM Tris-HCl at pH 7.5, 500 mM sodium chloride, 1 mM EDTA at pH 7.5 and 0.1% SDS. The oligo-dT column was then washed with 2 ml of 1×medium salt buffer consisting of 50 mM Tris-HCl at pH 7.5, 100 mM sodium chloride, 1 mM EDTA and 0.1% SDS. The messenger RNA was eluted from the oligo-dT column with 1 ml of buffer consisting of 10 mM Tris-HCl at pH 7.5, 1 mM EDTA at pH 7.5 and 0.05% SDS. The messenger RNA was purified by extracting this solution with phenol/chloroform followed by a single extraction with 100% chloroform. The messenger RNA was concentrated by ethanol precipitation and resuspended in DEPC H$_2$O.

The messenger RNA isolated by the above process contains a plurality of different $V_H$ and $V_L$ mRNA transcripts, i.e., greater than about 10$^4$ different $V_H$ and $V_L$ gene repertoires.

Example 3

Transcriptional Amplification of the $V_H$ Gene Repertoire

Transcriptional amplification is performed using the scheme as depicted in FIG. 4. In detail, about 5-10 µg of poly (A)$^+$ mRNAs in DEPC-treated water were first hybridized (annealed) with 1 µM antisense primer mixture comprising equal amounts of antisense EcoRI & stop codon-linked HJ$_H$ primers, for example, aHJ$_H$-1, 5'-dTGG AAT GAATTC G ATTGCTAG TCA GAC GGT GAC CAG GGT GCC-3' (SEQ ID NO:3); aHJ$_H$-2, 5'-dTGG AAT GAATTC GATTGCTAG TCA GAC GGT GAC CAT TGT CCC-3' (SEQ ID NO:4); aHJ$_H$-3, 5'-dTGG AAT GAATTC GATTGCTAG TCA GAC GGT GAC CAG GGT TCC-3' (SEQ ID NO:5); and aHJ$_H$-4, 5'-dTGG AAT GAATTC GATTGCTAG TCA GAC GGT GAC CGT GGT CCC-3' (SEQ ID NO:6) as listed in Table 1 (the EcoRI site and stop codons in three different frames are underlined), at 65° C. for 5 minutes and then cooled down to room temperature. The mixture was subsequently added to a reverse transcription (RT) reaction admixture (20 µl) on ice, comprising 2 µl of 10×buffer (400 mM Tris-HCl, pH 8.3 at 25° C., 300 mM KCl, 80 mM MgCl$_2$, 2 M betaine, 100 mM DTT), dNTPs (1.5 mM each for dATP, dGTP, dCTP and dTTP) and RNase inhibitors (20 U). After M-MuLV reverse transcriptase (40 U) was added, the reaction was incubated at 42° C. for 1 hour and shifted to 52° C. for another 15 min. The first-strand cDNAs so obtained were collected by a microcon-50 microconcentrater filter and then mixed with terminal transferase (50 U), dGTP (1.5 mM) in 0.5×buffer. The reaction was incubated at 37° C. for 15 min, stopped by denaturation at 94° C. for 3 min and instantly mixed with 1 µM sense T7 & NotI-linked primer of 5'-dCCA GTG AAT TGT AAT ACG ACT CAC TAT AGG GAA CGG CAT GGA AT GCGGCCG CCC CCC CCC C-3' (SEQ ID NO:57), the NotI site is underlined. After briefly centrifuging, Taq DNA polymerase (3.5 U) and dNTPs (1.5 mM each for dATP, dCTP and dTTP) were added to form T7 promoter-linked double-stranded cDNAs at 52° C. for 3 min and then 68° C. for 10 min. The resulting ds cDNAs comprise ds $V_H$ DNA homologs ready as template for RNA transcription amplification and in vitro transcription and translation. An in vitro transcription (IVT) reaction (40 µl) was prepared, containing 4 µl of 10×buffer, above reaction, rNTPs (2 mM each for ATP, GTP, CTP and UTP), and T7 RNA polymerase (160 U). After 1 hour incubation at 37° C., the amplified sense RNA transcripts were used directly for another round of amplification by repeating the above procedure, however, without the tailing reaction. The quality of amplified RNA library (2 µg) was assessed on a 1% formaldehyde-agarose gel. The resulting RNA transcripts can be translated into polypeptides of $V_H$ polypeptides.

The double stranded $V_H$ DNA homologs made by above protocol contain at the 5' end of the NotI restriction enzyme site and at the 3' end the EcoRI restriction site for cloning into a vector predigested with the NotI & EcoRI, in this instance, the Lambda ZAP II vector from Stratagene (La Jolla, Calif.) was predigested with NotI and EcoRI and the $V_H$ DNA homologs so made were digested with NotI and EcoRI and ligated into the Lambda ZAP II vector at the NotI and EcoRI sites. The $V_H$ DNA homologs so prepared also encode stop codons (UAA, UAG and UGA) in three different frames at the 3' end as in vitro and/or in vivo translation stop codons. The $V_H$ DNA homologs contain the 5' terminal sequences, such as the ribosome binding site, translation initiation site and ATG start codon, derived from the original heavy chain mRNA transcripts, and thus, can be ranslated into the $V_H$ polypeptides in vivo or in vitro directly.

The $V_H$ DNA homologs so made contain the T7 promoter sequence at the 5' end and can be further transcriptionally amplified by repeating the IVT procedure using the T7 RNA polymerase. The resulting ds $V_H$ DNA homologs can be the templates for further cloning process into either in vivo expression vector or in vitro transcription/translation unit sequences in the PROfusion or ribosome display methods.

Example 4

Transcriptional Amplification of the $V_K$ Gene Repertoire

In this example, the transcriptional amplification is performed using the scheme as depicted in FIG. 4. In detail, 5-10 µg of poly (A)$^+$ mRNAs in DEPC-treated water were first hybridized (annealed) with 1 µM antisense primer mixture comprising equal amounts of antisense XhoI & stop codon-linked HJ$_K$ primers, for example, aHJ$_K$-1, 5'-dTGG AAT T CTCGAGATTGCTAG TCA ACG TTT GAT TTC CAC CTT GGT CCC-3' (SEQ ID NO:24); aHJ$_K$-2, 5'-dTGG AAT T CTCGAGATTGCTAG TCA ACT TTT GAT CTC CAG CTT GGT CCC-3' (SEQ ID NO:25); aHJ$_K$-3, 5'-dTGG AAT T CTCGAGATTGCTAG TCA ACG TTT GAT ATC CAC TTT GGT CCC-3' (SEQ ID NO:26); aHJ$_K$-4, 5'-dTGG AAT T CTCGAGATTGCTAG TCA ACG TTT GAT CTC CAC CTT GGT CCC-3' (SEQ ID NO:27); and aHJ$_K$-5, 5'-dTGG AAT T CTCGAGATTGCTAG TCA ACG TTT AAT CTC CAG TCG TGT CCC-3' (SEQ ID NO:28) as listed in Table 2 (the XhoI site and stop codons in three different frames are underlined), at 65° C. for 5 minutes and then cooled down to room temperature. The mixture was subsequently added to a reverse transcription (RT) reaction admixture (20 µl) on ice, comprising 2 µl of 10×buffer (400 mM Tris-HCl, pH 8.3 at 25° C., 300 mM KCl, 80 mM MgCl$_2$, 2 M betaine, 100 mM DTT), dNTPs (1.5 mM each for dATP, dGTP, dCTP and dTTP) and RNase inhibitors (20 U). After M-MuLV reverse transcriptase (40 U) was added, the reaction was incubated at 42° C. for 1 hour and shifted to 52° C. for another 15 min. The first-strand cDNAs so obtained were collected by a microcon-50 microconcentrater filter and then mixed with terminal transferase (50 U), dGTP (1.5 mM) in 0.5×buffer. The reaction was incubated at 37° C. for 15 min, stopped by denaturation at 94° C. for 3 min and instantly mixed with 1 µM sense T7 & EcoRI-linked primer, for example, 5'-dCCA GTG AAT TGT AAT ACG ACT CAC TAT AGG GAA CGG CAT GGA ATGAATTCC CCC CCC CC-3' (SEQ ID NO:29). After briefly centrifuiging, Taq DNA polymerase (3.5 U) and dNTPs (1.5 mM each for dATP, dCTP and dTTP) were added and the mixture incubated at 52° C. for 3 min and then 68° C. for 10 min to form T7 promoter-linked double-stranded cDNAs. The resulting ds cDNAs comprise ds $V_K$ DNA homologs ready as template for RNA transcription amplification and in vitro transcription and translation. An in vitro transcription (IVT) reaction (40 µl) was prepared, containing 4 µl of 10×buffer, above reaction, rNTPs (2 mM each for ATP, GTP, CTP and UTP), and T7 RNA polymerase (160 U). After 1 hour incubation at 37° C., the amplified sense RNA transcripts were used directly for another round of amplification by repeating the above procedure, however, without the tailing reaction. The quality of amplified RNA library (2 µg) was assessed on a 1% formaldehyde-agarose gel. The resulting RNA transcripts can be translated into polypeptides of $V_K$ polypeptides.

The double stranded $V_K$ DNA homologs made by above protocol contain at the 5' end an EcoRI restriction enzyme site and at the 3' end an XhoI restriction site for cloning into a vector predigested with the EcoRI and XhoI, for example, the Lambda ZAP II vector from Stratagene (La Jolla, Calif.) was predigested with EcoRI and XhoI, and the $V_K$ DNA homologs so made were digested with EcoRI and XhoI and ligated into the Lambda ZAP II vector at the EcoRI and XhoI sites. The $V_K$ DNA homologs so prepared also encode stop codons (UAA, UAG and UGA) in three different frames at the 3' end as in vitro and/or in vivo translation stop codons. The $V_K$ DNA homologs contain 5' terminal sequences such as the ribosome binding site, transtation initiation site and ATG start codon derived from the original light kappa chain mRNA transcripts, and thus, can be translated into the $V_K$ polypeptides in vivo or in vitro directly.

The $V_K$ DNA homologs so made contain the T7 promoter sequence at the 5' end and can be further transcriptionally amplified by repeating the IVT using the T7 RNA polymerase. The resulting ds $V_K$ DNA homologs can be the templates for further cloning into either an in vivo expression vector or in an in vitro transcription/translation system such as in the PROfusion or ribosome display methods.

Example 5

Transcriptional Amplification of the $V_\lambda$ Gene Repertoire

In this example, the transcriptional amplification is performed using the scheme as depicted in FIG. 4. In detail, about 5-10 µg of poly (A)⁺ mRNAs in DEPC-treated water were first hybridized (annealed) with 1 µM antisense primer mixture comprising equal amounts of antisense XhoI & stop codon-linked $HJ_\lambda$ primers, for example, $aHJ_\lambda$-1, 5'-dTGG AAT TCTCGAGATTGCTAG TCA ACC TAG GAC GGT GAC CTT GGT CCC-3' (SEQ ID NO:41); $HJ_\lambda$-2, 5'-dTGG AAT CTCGAGATTGCTAG TCA ACC TAG GAC GGT CAG CTT GGT CCC-3' (SEQ ID NO:42); and $HJ_\lambda$-3, 5'-dTGG AAT TCTCGAGATTGCTAG TCA ACC TAA AAC GGT GAG CTG GGT CCC-3' (SEQ ID NO:43) as listed in Table 3 (the XhoI site and the stop codons in three different frames are underlined), at 65° C. for 5 minutes and then cooled down to room temperature. The mixture was subsequently added to a reverse transcription (RT) reaction admixture (20 µl) on ice, comprising 2 µl of 10×buffer (400 mM Tris-HCl, pH 8.3 at 25° C., 300 mM KCl, 80 mM $MgCl_2$, 2 M betaine, 100 mM DTT), dNTPs (1.5 mM each for dATP, dGTP, dCTP and dTTP) and RNase inhibitors (20 U). After M-MuLV reverse transcriptase (40 U) was added, the reaction was incubated at 42° C. for 1 hour and shifted to 52° C. for another 15 min. The first strand cDNAs so obtained were collected by a microcon-50 microconcentrater filter and then mixed with terminal transferase (50 U), dGTP (1.5 mM) in 0.5×buffer. The reaction was incubated at 37° C. for 15 min, stopped by denaturation at 94° C. for 3 min and instantly mixed with 1 µM sense T7 & EcoRI-linked primer, such as 5'-dCCA GTG AAT TGT AAT ACG ACT CAC TAT AGG GAA CGG CAT GGA ATGAATTCC CCC CCC CC-3' (SEQ ID NO:44). After briefly centrifuging, Taq DNA polymerase (3.5 U) and dNTPs (1.5 mM each for dATP, dCTP and dTTP) were added and the mixture incubated at 52° C. for 3 min and then 68° C. for 10 min to form T7 promoter-linked double-stranded cDNAs. The resulting ds cDNAs comprise ds $V_\lambda$ DNA homologs ready as template for RNA transcription amplification and in vitro transcription and translation. An in vitro transcription (IVT) reaction (40 µl) was prepared, containing 4 µl of 10×buffer, above reaction, rNTPs (2 mM each for ATP, GTP, CTP and UTP), and T7 RNA polymerase (160 U). After one hour incubation at 37° C., the amplified sense RNA transcripts were used directly for another round of amplification by repeating the above procedure, however, without the tailing reaction. The quality of amplified RNA library (2 µg) was assessed on a 1% formaldehyde-agarose gel. The resulting RNA transcripts can be translated into polypeptides of $V_\lambda$ polypeptides.

The double stranded $V_\lambda$ DNA homologs made by above protocol contain at the 5' end an EcoRI restriction enzyme site and at the 3' end, an XhoI restriction site for cloning into a vector predigested with the EcoRI and XhoI. For example, the Lambda ZAP II vector from Stratagene (La Jolla, Calif.) was predigested with EcoRI and XhoI and the $V_\lambda$ DNA homologs so made were digested with EcoRI and XhoI, and ligated into the Lambda ZAP II vector at the EcoRI and XhoI sites. The $V_\lambda$ DNA homologs so prepared also encode stop codons (UAA, UAG and UGA) in three different frames at the 3' end and are in vitro and/or in vivo translation stop codons. The $V_\lambda$ DNA homologs contains 5' sequences such as ribosome binding site, translation initiation site and ATG start codon derived from the original light lambda chain mRNA transcripts. Thus, the instant clones can be translated into the $V_\lambda$ polypeptides in vivo or in vitro directly.

The $V_\lambda$ DNA homologs so made contain the T7 promoter sequence at the 5' end and can be further transcriptionally amplified by repeating the IVT using the T7 RNA polymerase. The resultant ds $V_\lambda$ DNA homologs can be the templates for further cloning into either in vivo expression vector or in vitro transcription/translation unit sequences in the PROfusion or ribosome display methods.

Example 6

Human $V_H$ Expression Phage Library Construction

The Lambda ZAP II™ vector from Stratagene (La Jolla, Calif.) (Short et al., Nucleic Acids Res., 16:7583-7600, 1988) was used as an example of an expression vector system for constructing the $V_H$-expressing library. The Lambda ZAP II™ vector is well known to the skilled in the art as a phage vector that can be efficiently packaged in vitro and reintroduced into bacterial host cells. The expressed protein therefrom can be detected at the level of single phage plaques. The signal to noise ratio for screening of phage libraries is very high with very low nonspecific binding. Finally, the vector can be converted by in vivo excision into a phagemid vector for further analysis such as such as sequencing analysis of isolated clones.

Figure 7:
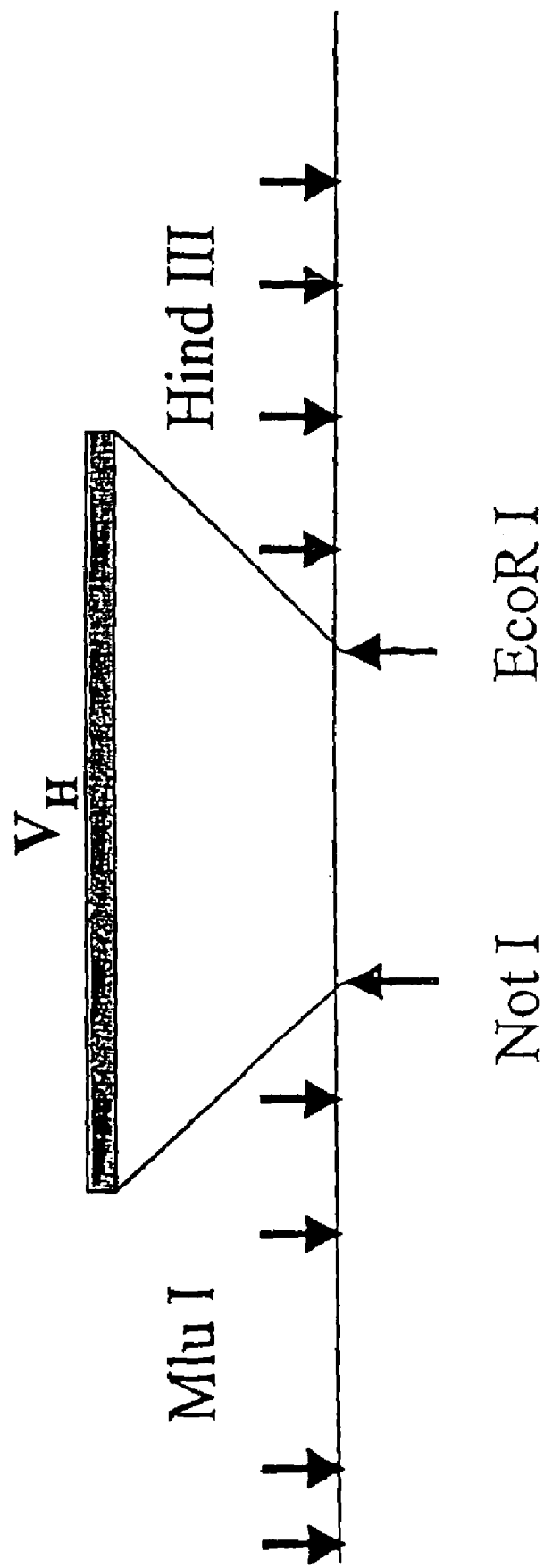
FIG. 7 illustrates a schematic diagram for making a $V_H$ phage library.

To prepare an expression library of the $V_H$ gene repertoire as depicted in FIG. 7, the $V_H$ DNA homologs enriched in $V_H$ gene repertoire sequences were prepared according to Example 3. These double stranded $V_H$ DNA homologs, containing NotI and EcoRI restriction enzyme sites, were digested with the restriction enzymes NotI and EcoRI. The digested $V_H$ DNA homologs were subject to electrophoresis and purified on a 1% agarose gel using the standard electroelution technique described in "Molecular Cloning: A Laboratory Manual", Maniatis et al., eds., Cold Spring Harbor, N.Y., (1982). The region of the gel containing DNA fragments of approximately 350 bps was excised, electroeluted into a dialysis membrane, ethanol precipitated and resuspended in 10 mM Tris-HCl pH 7.5 and 1 mM EDTA to a final concentration of 10 ng/ul. Equimolar amounts of the $V_H$ DNA homologs insert were then ligated overnight at 5° C. to 1 μg of Lambda ZAP II vector previously cut by EcoRI and NotI. The ligation mixture containing the $V_H$ DNA homologs were packaged according to the manufacturer specifications using Gigapack Gold II Packing Extract (Stratagene Cloning Systems, La Jolla, Calif.). The expression libraries were then ready to be plated on XL-1 Blue cells.

Example 7

Human $V_K$ Expression Phage Library Construction

Figure 8:
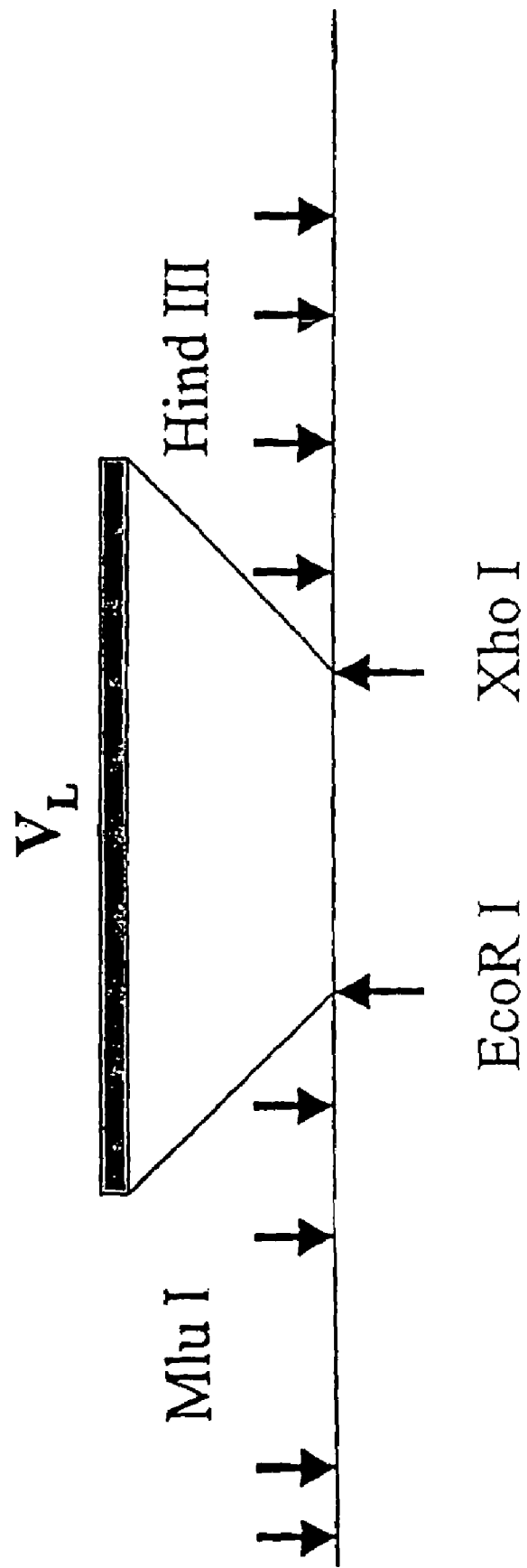
FIG. 8 illustrates a schematic diagram for making a $V_L$ ($V_K$ and $V_\lambda$) phage library.

To prepare an expression library of the $V_K$ gene repertoire as depicted in FIG. 8, the $V_K$ DNA homologs enriched in $V_K$ gene repertoire sequences were prepared according to Example 4. These double stranded $V_K$ DNA homologs, containing EcoRI and XhoI restriction enzyme sites, were digested with the restriction enzymes EcoRI and XhoI. The digested $V_K$ DNA homologs were subjected to electrophoresis and purified on a 1% agarose gel using the standard electroelution technique described in "Molecular Cloning: A Laboratory Manual", Maniatis et al., eds., Cold Spring Harbor, N.Y., (1982). The region of the gel containing DNA fragments of approximately 350 bps was excised, electroeluted into a dialysis membrane, ethanol precipitated and resuspended in 10 mM Tris-HCl pH 7.5 and 1 mM EDTA to a final concentration of 10 ng/ul. Equimolar amounts of the $V_K$ DNA homologs insert were then ligated overnight at 5° C. to 1 μg of Lambda ZAP II vector previously cut by EcoRI and XhoI. The ligation mixture containing the $V_K$ DNA homologs were packaged according to the manufacturer specifications using Gigapack Gold II Packing Extract (Stratagene Cloning Systems, La Jolla, Calif.). The expression libraries were then ready to be plated on XL-1 Blue cells.

Example 8

Human $V_\lambda$ Expression Phage Library Construction

To prepare an expression library of the $V_\lambda$ gene repertoire, the $V_\lambda$ DNA homologs enriched in $V_\lambda$ gene repertoire sequences were prepared according to Example 5. These double stranded $V_\lambda$ DNA homologs, containing EcoRI and XhoI restriction enzyme sites, were digested with the restriction enzymes EcoRI and XhoI. The digested $V_\lambda$ DNA homologs were subject to electrophoresis and purified on a 1% agarose gel using the standard electroelution technique described in "Molecular Cloning: A Laboratory Manual", Maniatis et al., eds., Cold Spring Harbor, N.Y., (1982). The region of the gel containing DNA fragments of approximately 350 bps was excised, electroeluted into a dialysis membrane, ethanol precipitated and resuspended in 10 mM Tris-HCl pH 7.5 and 1 mM EDTA to a final concentration of 10 ng/ul. Equimolar amounts of the $V_\lambda$ DNA homologs insert were then ligated overnight at 5° C. to 1 ug of Lambda ZAP II vector previously cut by EcoRI and XhoI. The ligation mixture containing the VA DNA homologs were packaged according to the manufacturers specifications using Gigapack Gold II Packing Extract (Stratagene Cloning Systems, La Jolla, Calif.). The expression libraries were then ready to be plated on XL-1 Blue cells.

Example 9

Human $V_H$+$V_L$ Combinatorial Antibody Expression Phage Library Construction

Figure 9:
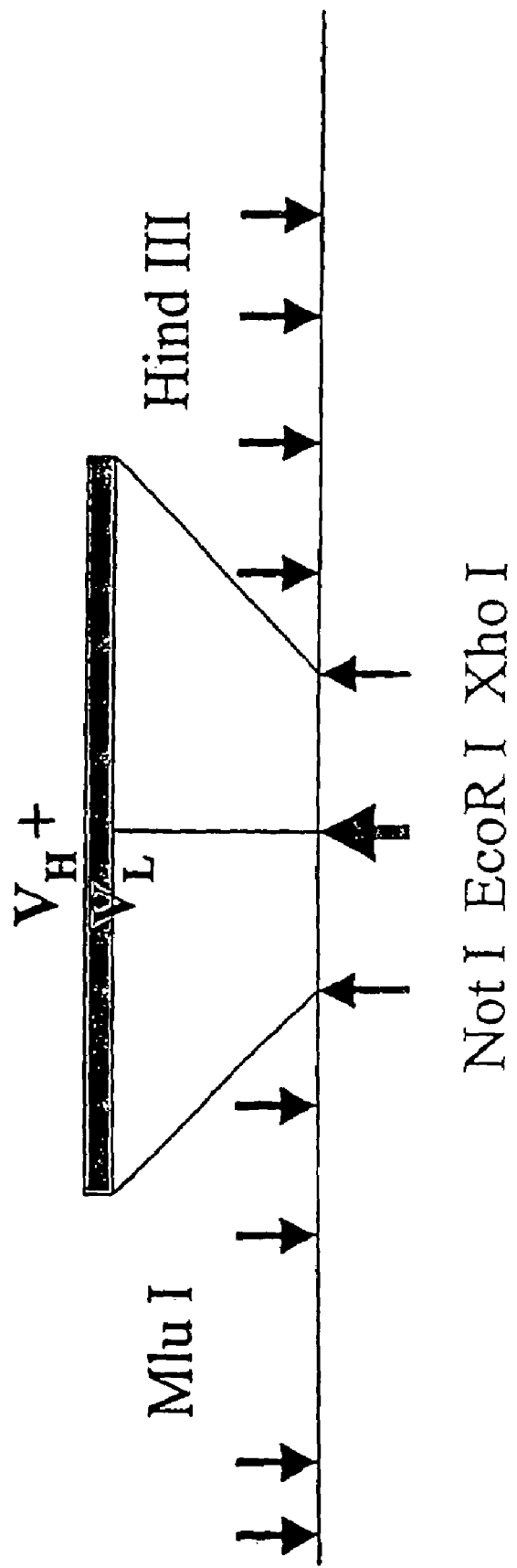
FIG. 9 illustrates a schematic diagram for constructing a $V_H$+$V_L$ phage library.

The construction of a combinatorial library of human antibodies was accomplished by combining the $V_H$ library made in Example 6 with either one or both of the $V_K$ library made in Example 7 and the $V_\lambda$ library made in Example 8 at the symmetric EcoRI sites present in each vector as depicted in FIG. 9. This resulted in a library of clones, each of which potentially co-expresses a $V_H$ and a $V_L$ gene on a single transcript chain. And each host cell may express a heterodimeric antibody consisting of a $V_H$ polypeptide and $V_L$ polypeptide.

The phage library DNA of $V_H$ and $V_L$ ($V_\kappa$ and $V_\lambda$) was first purified from each library. The phage libraries prepared in Example 6, 7 and 8 were amplified and 500 μg of phage library DNA prepared from the amplified phage stock using the procedures described in "Molecular Cloning: A Laboratory Manual", Maniatis et al., eds., Cold Spring Harbor Laboratory, Cold Spring Harbor, N.Y. (1982).

To accomplish the cross at the EcoRI site as depicted in FIG. 9, the $V_H$ phage library DNA as made according to Example 6 was digested with HindIII, the resulting 5' ends dephosphorylated and the product further digested with EcoRI. This process cleaved the right arm of the Lambda ZAPII vector into several pieces but the left arm containing the $V_H$ sequences, remained intact. Fifty (50) μg of $V_H$-expression library phage DNA were maintained in a solution containing 100 units of HindIII (Boehringer Mannheim, Indianapolis, Ind.) in 200 μl of a buffer supplied by the endonuclease manufacturer for 1.5 hours at 37° C. The solution was then extracted with a mixture of phenol and chloroform. The DNA was then ethanol precipitated and resuspended in 100 μl of water. This solution was admixed with 100 units of the restriction endonuclease EcoRI (Boehringer Mannheim, Indianapolis, Ind.) in a final volume of 200 μl of buffer containing the components specified by the manufacturer. This solution was maintained at 37° C. for 1.5 hours and the solution was then extracted with a mixture of phenol and chloroform. The DNA was ethanol precipitated and the DNA resuspended in TE.

In a parallel fashion, the phage library DNA of $V_L$ ($V_K$ and $V_\lambda$) was digested with MluI, dephosphorylated and further digested with EcoRI, destroying the left arm of the Lambda ZAPII but leaving the right arm containing the $V_L$ sequences intact. The $V_L$ expression library prepared in Example 7 (the $V_K$) and Example 8 (the $V_\lambda$) were amplified. Twenty five (25) μg of each of the $V_K$ and $V_\lambda$ expression library phage DNAs were mixed and maintained in a solution containing 100 units of MluI restriction endonuclease (Boehringer Mannheim, Indianapolis, Ind.) in 200 μl of a buffer supplied by the endonuclease manufacturer for 1.5 hours at 37° C. The solution was then extracted with a mixture of phenol and chloroform saturated with 0.1 M Tris-HCl at pH 7.5. The DNA was then ethanol precipitated and resuspended in 100 μl of water. This solution was admixed with 100 units of EcoRI (Boehringer Mannheim, Indianapolis, Ind.) in a final volume of 200 μl of buffer containing the components specified by the manufacturer. This solution was maintained at 37° C. for 1.5 hours and the solution was then extracted with a mixture of phenol and chloroform. The DNA was ethanol precipitated and the DNA resuspended in TE.

The restriction digested $V_H$ and $V_L$ expression libraries were ligated together. The ligation reaction consisted of 1 μg of $V_H$ and 1 μg of $V_L$ phage library DNA in a 10 μl reaction using the reagents supplied in a ligation kit purchased from Stratagene Cloning Systems (La Jolla, Calif.). After ligation, only clones which resulted from combination of a left arm of $V_H$-containing clones and a right arm of $V_L$-containing clones reconstituted a viable phage. The ligation mixture containing the $V_H$+$V_L$ DNA homologs were packaged according to the specifications of the manufacturer using the Gigapack Gold II Packing Extract (Stratagene Cloning Systems, La Jolla, Calif.). The $V_H+V_L$-expressing libraries were then ready to be plated on XL-1 Blue cells.

Example 10

Single Chain Human Antibody Library Construction

Figure 10:
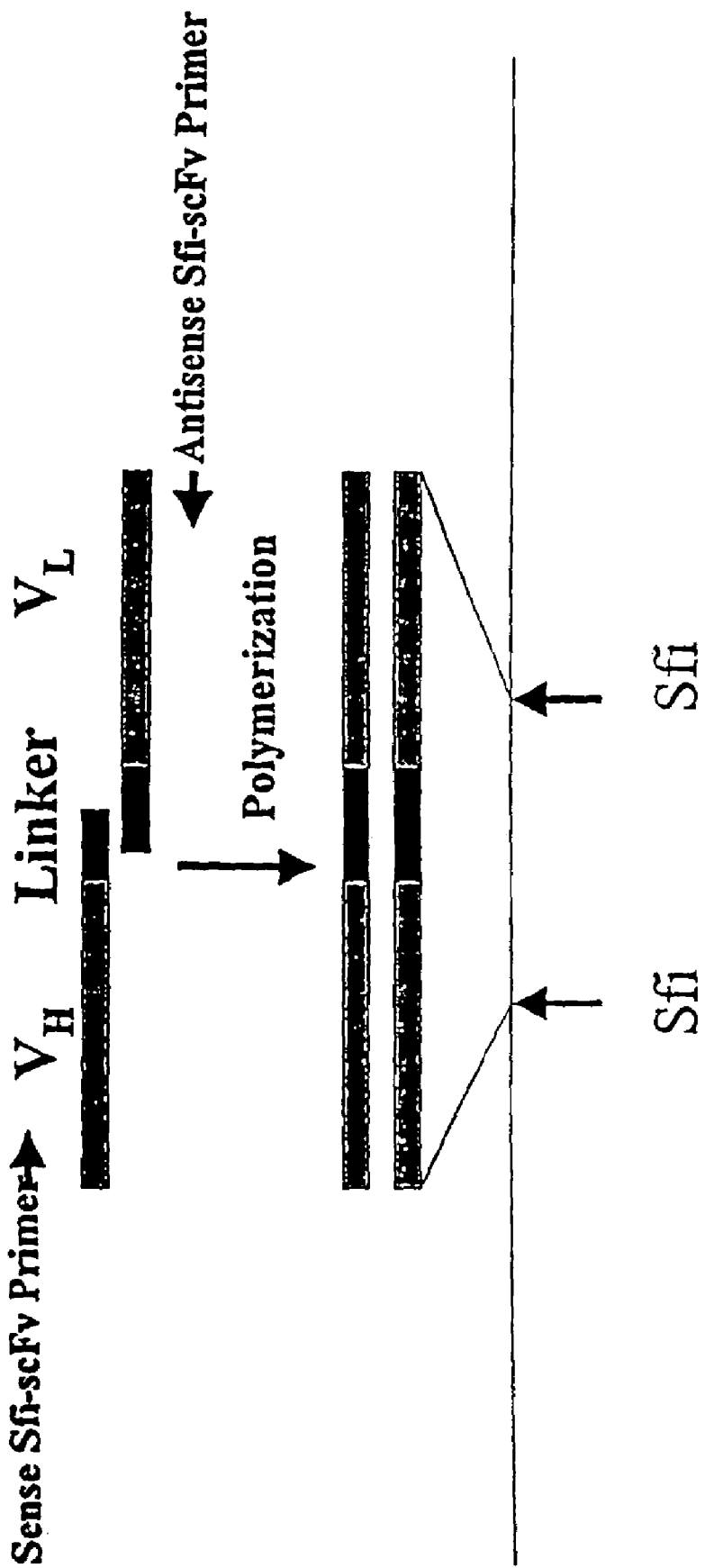
FIG. 10 illustrates a schematic diagram for generating an sc$F_v$ DNA homologs.

The single chain antibody or $scF_v$ typically has a linker peptide such as (GlyGlyGlyGlySer (SEQ ID NO:1))$_n$ linking the $V_H$ and $V_L$ genes. The construction of an $scF_v$ human antibody library can be made by linking the $V_H$ and $V_L$ DNA homologs together with a sequence encoding a linking peptide and inserting the single chain ($V_H$+linker+$V_L$) into an appropriate expression vector or in vitro transcription/translation unit sequence as depicted in FIG. 10.

The amplification strategy for the $V_H$ and $V_L$ ($V_K$ and $V_\lambda$) DNA homologs is depicted in FIG. 2, wherein the sequence-specific antisense primers are linked with a T7 RNA promoter sequence and the sense primers are sequence-specific primers. The antisense primers for the $V_H$ DNA homologs and the sense sequence-specific primers for the $V_L$ have incorporated the linker sequence so that the $V_H$ and $V_L$ DNA homologs can be overlapped and operatively linked by the linker sequence into a single chain sequence of $V_H+V_L$ DNA homologs. The single chain $V_H+V_L$ DNA homologs can be amplified with two flanking primers with appropriate restriction enzyme sites for inserting into an appropriate expression vector or in vitro transcription/translation unit for expressing the $scF_v$ antibody.

The transcriptional amplification of the $V_H$ gene is performed using the scheme as depicted in FIG. 2. In detail, about 5-10 µg of poly (A)$^+$ mPNAs in DEPC-treated water were first hybridized (annealed) with 1 µM antisense primer mixture comprising equal amounts of T7 & peptide linker (PL)-linked antisense T7 $HJ_H$ primers, such as aT7PLHJ$_H$-1 (5'-dCCAGTGAATTGTAATACGACTCACTATAGGGAA AGA GCC GCC GCC GCC TGA GGA GAC GGT GAC CAG GGT GCC-3') (SEQ ID NO:8); aT7PLHJ$_H$-2 (5'-d CCAGTGAATTGTAATACGACTCACTATAGGGAA AGA GCC GCC GCC GCC TGA GGA GAC GGT GAC CAT TGT CCC-3') (SEQ ID NO:9); aT7PLHJ$_H$-3 (5'-d CCAGTGAATTGTAATACGACTCACTATAGGGAA AGA GCC GCC GCC GCC TGA GGA GAC GGT GAC CAG GGT TCC-3') (SEQ ID NO:10); and aT7PLHJ$_H$-4 (5'-d CCAGTGAATTGTAATACGACTCACTATAGGGAA AGA GCC GCC GCC GCC TGA GGA GAC GGT GAC CGT GGT CCC-3') (SEQ ID NO:11) as in Table 1 (the overlapping peptide linker is underlined), at 65° C. for 5 minutes and cooled to room temperature. The mixture was subsequently added to a reverse transcription (RT) reaction admixture (20 µl) on ice, comprising 2 µl of 10×buffer (400 mM Tris-HCl, pH 8.3 at 25° C., 300 mM KCl, 80 mM MgCl$_2$, 2 M betaine, 100 mM DTT), dNTPs (1.5 mM each for dATP, dGTP, dCTP and dTTP) and RNase inhibitors (20 U). After M-MuLV reverse transcriptase (40 U) was added, the reaction was incubated at 42° C. for 1 hour and shifted to 52° C. for another 15 min. The first-strand cDNAs so obtained were collected by a microcon-50 microconcentrater filter. The resultant purified first strand cDNAs were denatured from the mRNAs by denaturation at 94° C. for 3 min and instantly mixed with 1 µM of a sense HV$_H$ primer mixture comprising equal amounts of sense HV$_H$ primers such as sHV$_H$-1 (5'-CAG CCG GCC ATG GCA CAG GTN CAG CTG GTR CAG TCT GG-3') (SEQ ID NO:12); sHV$_H$-2 (5'-CAG CCG GCC ATG GCA CAG GTC CAG CTG GTR CAG TCT GGG G-3') (SEQ ID NO:13); sHV$_H$-3 (5'-CAG CCG GCC ATG GCA CAG GTK CAG CTG GTG SAG TCT GGG-3') (SEQ ID NO:14); sHV$_H$-4 (5'-CAG CCG GCC ATG GCA CAG GTC ACC TTG ARG GAG TCT GGT CC-3') (SEQ ID NO:15); sHV$_H$-5 (5'-CAG CCG GCC ATG GCA CAG GTG CAG CTG GTG GAG WCT GG-3') (SEQ ID NO:16); sHV$_H$-6 (5'-CAG CCG GCC ATG GCA CAG GTG CAG CTG GTG SAG TCY GG-3') (SEQ ID NO:17); sHV$_H$-7 (5'-CAG CCG GCC ATG GCA CAG GTG CAG CTG CAG GAG TCG G-3') (SEQ ID NO:18); sHV$_H$-8 (5'-CAG CCG GCC ATG GCA CAG GTG CAG CTG TTG SAG TCT G-3') (SEQ ID NO:19); sHV$_H$-9 (5'-CAG CCG GCC ATG GCA CAG GTG CAG CTG GTG CAA TCT G-3'), (SEQ ID NO:20); sHV$_H$-10 (5'-CAG CCG GCC ATG GCA CAG GTG CAG CTG CAG GAG TCC GG-3') (SEQ ID NO:21); sHV$_H$-11 (5'-CAG CCG GCC ATG GCA CAG GTG CAG CTA CAG CAG TGG G-3') (SEQ ID NO:22); and sHV$_H$-12 (5'-CAG CCG GCC ATG GCA CAG GTA CAG CTG CAG CAG TCA G-3') (SEQ ID NO:23).

After briefly centrifuging, Taq DNA polymerase (3.5 U) and dNTPs (1.5 mM each for dATP, dCTP, dGTP and dTTP) were added to form promoter-linked double-stranded cDNAs at 52° C. for 3 min and then 68° C. for 10 min. An in vitro transcription (IVT) reaction (40 µl) was prepared, containing 4 µl of 10×buffer, rNTPs (2 mM each for ATP, GTP, CTP and UTP), and T7 RNA polymerase (160 U). After 1 hour incubation at 37° C., the amplified antisense $V_H$ RNA transcripts were directly used for making the double stranded $V_H$ DNA homologs. The antisense RNA transcripts were purified and collected by a microcon-50 microconcentrater filter and then subjected to a reverse transcription (RT) reaction admixture (20 µl), comprising 2 µl of 10×buffer, 1 µM sense HV$_H$ primers as described in the above paragraph, dNTPs (1.5 mM each for dATP, dGTP, dCTP and dTTP) and RNase inhibitors (20 U). After M-MuLV reverse transcriptase (40 U) was added, the reaction was incubated at 42° C. for 1 hour and shifted to 52° C. for another 15 min. The sense orientation first-strand cDNAs so obtained were collected by a microcon-50 microconcentrater filter. The resulting purified sense orientation first strand cDNAs were denatured from the antisense RNA transcripts by denaturation at 94° C. for 3 min and instantly mixed with 1 µM of a T7 & peptide linker-linked antisense HJ$_H$ primer mixture as described in the above paragraph. After briefly centrifuging, Taq DNA polymerase (3.5 U) and dNTPs (1.5 mM each for dATP, dCTP, dGTP and dTTP) were added to form promoter-linked double-stranded cDNAs at 52° C. for 3 min and then 68° C. for 10 min.

The resulting ds $V_H$ DNA homologs can be further transcriptionally amplified by repeating the IVT using the T7 RNA polymerase. The resultant ds $V_H$ DNA homologs can be the templates for further cloning and processing into either an in vivo expression vector or an in vitro transcription/translation system as in the PROfusion or ribosome display method.

In the case of making the $scF_v$ antibody the antisense amplified $V_H$ RNA transcripts made by the steps above can be used as the template for making single stranded sense $V_H$ sequences by using a single sense primer sequence, such as, the sense Sfi-scF$_v$ primer of 5'-TTG TTA TTA CTC GCG GCC CAG CCG GCC ATG GCA CAG GT-3' (SEQ ID NO. 55) (Table 4) in a reverse transcription reaction. Briefly, the antisense RNA transcripts were purified and collected by a microcon-50 microconcentrate filter and then subjected to the reverse transcription (RT) reaction admixture (20 µl), comprising 2 µl of 10×buffer, 1 µM sense Sfi-scF$_v$ primer as described in the above, dNTPs (1.5 mM each for dATP, dGTP, dCTP and dTTP) and RNase inhibitors (20 U). After M-MuLV reverse transcriptase (40 U) was added, the reaction was incubated at 42° C. for 1 hour and shifted to 52° C. for another 15 min. The sense-orientation first-strand cDNAs so obtained were collected by a microcon-50 microconcentrater filter. The resulting purified sense orientation first strand cDNAs were denatured from the antisense RNA transcripts by denaturation at 94° C. for 3 min. The single stranded antisense $V_H$ DNA sequences were then used in an overlapping strand extension reaction with the single-stranded antisense $V_L$ DNA sequences as described below.

The transcriptional amplification of a $V_K$ gene is performed using the scheme as depicted in FIG. 2. In detail, about 5-10 μg of poly (A)+ mRNAs in DEPC-treated water were first hybridized (annealed) with 1 μM antisense primer mixture comprising equal amounts of T7-linked antisense $HJ_K$ primers such as $aT7HJ_K$-1 (5'-d CCAGTGAATTGTAATACGACTCACTATAGGGAA TGG AAT TCG GCC CCC GAG GCC ACG TTT GAT TTC CAC CTT GGT CCC-3') (SEQ ID NO:30); $aT7HJ_K$-2 (5'-d CCAGTGAATTGTAATACGACTCACTATAGGGAA TGG AAT TCG GCC CCC GAG GCC ACG TTT GAT CTC CAG CTT GGT CCC-3') (SEQ ID NO:31); $aT7HJ_K$-3 (5'-d CCAGTGAATTGTAATACGACTCACTATAGGGAA TGG AAT TCG GCC CCC GAG GCC ACG TTT GAT ATC CAC TTT GGT CCC-3') (SEQ ID NO:32); $aT7HJ_K$-4 (5'-d CCAGTGAATTGTAATACGACTCACTATAGGGAA TGG AAT TCG GCC CCC GAG GCC ACG TTT GAT CTC CAC CTT GGT CCC-3') (SEQ ID NO:33); and $aT7HJ_K$-5 (5'-d CCAGTGAATTGTAATACGACTCACTATAGGGAA TGG AAT TCG GCC CCC GAG GCC ACG TTT AAT CTC CAG TCG TGT CCC-3') (SEQ ID NO:34) (Table 2), at 65° C. for 5 minutes and cooled down to room temperature. The reaction was subsequently were added to a reverse transcription (RT) reaction admixture (20 μl) on ice, comprising 2 μl of 10×buffer (400 mM Tris-HCl, pH 8.3 at 25° C., 300 mM KCl, 80 mM MgCl$_2$, 2 M betaine, 100 mM DTT), the above reaction mixture, dNTPs (1.5 mM each for dATP, dGTP, dCTP and dTTP) and RNase inhibitors (20 U). After M-MuLV reverse transcriptase (40 U) was added, the reaction was incubated at 42° C. for 1 hour and shifted to 52° C. for another 15 min. The first-strand cDNAs so obtained were collected by a microcon-50 microconcentrater filter. The resulting purified first strand cDNAs were denatured from the mRNAs by denaturation at 94° C. for 3 min and instantly mixed with 1 μM of sense $HV_K$ primers such as sense peptide linker-linked $HV_K$ primers such as $sPLHV_K$-1 (5'-TCC TCA GGC GGC GGC GGC TCT GGC GGA GGT GGC AGC GGC GGT GGC GGA TCC GAC ATC CAG ATG ACC CAG TCT CC-3') (SEQ ID NO:35); $sPLHV_K$-2 (5'-TCC TCA GGC GGC GGC GGC TCT GGC GGA GGT GGC AGC GGC GGT GGC GGA TCC GAT GTT GTG ATG ACT CAG TCT CC-3') (SEQ ID NO:36); $sPLHV_K$-3 (5'-TCC TCA GGC GGC GGC GGC TCT GGC GGA GGT GGC AGC GGC GGT GGC GGA TCC GAA ATT GTG TTG ACG CAG TCT CC-3') (SEQ ID NO:37); $sPLHV_K$-4 (5'-TCC TCA GGC GGC GGC GGC TCT GGC GGA GGT GGC AGC GGC GGT GGC GGA TCC GAC ATC GTG ATG ACC CAG TCT CC-3') (SEQ ID NO:38); $sPLHV_K$-5 (5'-TCC TCA GGC GGC GGC GGC TCT GGC GGA GGT GGC AGC GGC GGT GGC GGA TCC GAA ACG ACA CTC ACG CAG TCT CC-3') (SEQ ID NO:39); and $sPLHV_K$-6 (5'-GGC AGC GGC GGT GGC GGA TCC GAA ATT GTG CTG ACT CAG TCT CC-3') (SEQ ID NO:58) (Table 2). After briefly centrifuging, Taq DNA polymerase (3.5 U) and dNTPs (1.5 mM each for dATP, dCTP, dGTP and dTTP) were added to form promoter-linked double-stranded cDNAs at 52° C. for 3 min and then 68° C. for 10 min. An in vitro transcription (IVT) reaction (40 μl) was prepared, containing 4 μl of 10× buffer, above reaction, rNTPs (2 mM each for ATP, GTP, CTP and UTP), and T7 RNA polymerase (160 U). After one hour incubation at 37° C., the antisense amplified $V_K$ RNA transcripts were directly used for making the double stranded $V_K$ DNA homologs. The antisense RNA transcripts were purified and collected by a microcon-50 microconcentrater filter and then subjected to reverse transcription (RT) (20 μl), comprising 2 μl of 10×buffer, 1 μM sense peptide linker-linked $HV_K$ primers of above, dNTPs (1.5 mM each for dATP, dGTP, dCTP and dTTP) and RNase inhibitors (20 U). After M-MuLV reverse transcriptase (40 U) was added, the reaction was incubated at 42° C. for 1 hour and shifted to 52° C. for another 15 min. The sense orientation first strand cDNAs so obtained were collected by a microcon-50 microconcentrater filter. The resulting purified sense orientation first strand cDNAs were denatured from the antisense RNA transcripts by denaturation at 94° C. for 3 min and instantly mixed with 1 μM T7-linked antisense HJk primers mixture as described above. After briefly centrifuging, Taq DNA polymerase (3.5 U) and dNTPs (1.5 mM each for dATP, dCTP, dGTP and dTTP) were added and incubated at 52° C. for 3 min and then 68° C. for 10 min to form promoter-linked double-stranded cDNAs.

The resulting ds $V_K$ DNA homologs can be further transcriptionally amplified by repeating the IVT using T7 RNA polymerase. The resulting ds $V_K$ DNA homologs can be the templates for further cloning and processing in either an in vivo expression vector or in an in vitro transcription/translation unit system such as the PROfusion or ribosome display method.

In the case of making an $scF_v$ antibody, the $V_K$ DNA homologs made by the steps above can be used as the template for making single stranded antisense $V_K$ sequences by using a single antisense primer sequence, such as the antisense Sfi-$scF_v$ primer, 5'-GTC CTC GTC GAC TGG AAT TCG GCC CCC GAG GCC AC-3' (SEQ ID NO:56) (Table 4) in a primer extension reaction. Briefly, the $V_K$ DNA homologs (20 ng) made above was added to an admixture of 1 μM of the antisense primer above, Taq DNA polymerase (3.5 U) and dNTPs (1.5 mM each for dATP, dCTP, dGTP and dTTP), were combined and the mixture was denatured at 94° C. for 5 min., then followed by five cycles of 1 min at 94° C., 1 min. at 60° C. and 1.5 min at 72° C. The single stranded antisense $V_K$ DNA sequences were then used in an overlapping strand extension reaction with the single-stranded sense $V_H$ DNA sequences made as described above in a reaction as described below.

The transcriptional amplification of a $V_\lambda$ gene is performed using the scheme as depicted in FIG. 2. In detail, about 5-10 μg of poly (A)+ mRNAs in DEPC-treated water were first hybridized (annealed) with 1 μM antisense primer mixture comprising equal amounts of, for example, T7-linked antisense $HJ_\lambda$ primers such as $aT7HJ_\lambda$-1 (5'-d CCAGTGAATTGTAATACGACTCACTATAGGGAA TGG AAT TCG GCC CCC GAG GCC ACC TAG GAC GGT GAC CTT GGT CCC-3') (SEQ ID NO:45); $aT7HJ_\lambda$-2 (5'-d CCAGTGAATTGTAATACGACTCACTATAGGGAA TGG AAT TCG GCC CCC GAG GCC ACC TAG GAC GGT CAG CTT GGT CCC-3') (SEQ ID NO:46); and $aT7HJ_\lambda$-3 (5'-d CCAGTGAATTGTAATACGACTCACTATAGGGAA TGG AAT TCG GCC CCC GAG GCC ACC TAA AAC GGT GAG CTG GGT CCC-3') (SEQ IN NO:47) at 65° C. for five minutes and cooled down to room temperature. The reaction was subsequently added to a reverse transcription (RT) reaction admixture (20 μl) on ice, comprising 2 μl of 10×buffer (400 mM Tris-HCl, pH 8.3, 300 mM KCl, 80 mM MgCl$_2$, 2 M betaine, 100 mM DTT), dNTPs (1.5 mM each for dATP, dGTP, dCTP and dTTP) and RNase inhibitors (20 U). After M-MuLV reverse transcriptase (40 U) was added, the reaction was incubated at 42° C. for 1 hour and shifted to 52° C. for another 15 min. The first strand cDNAs so obtained were collected by a microcon-50 microconcentrater filter. The resulting purified first strand cDNAs were denatured from the mRNAs by denaturation at 94° C. for 3 min and instantly mixed with 1 µM sense $HV_\lambda$ primers comprising for example, equal amounts of sense peptide linker-linked $HV_\lambda$ primers, sPLHV$_\lambda$-1 (5'-TCC TCA GGC GGC GGC GGC TCT GGC GGA GGT GGC AGC GGC GGT GGC GGA TCC CAG TCT GTG TTG ACG CAG CCG CC-3') (SEQ ID NO:48); sPLHV$_\lambda$-2 (5'-TCC TCA GGC GGC GGC GGC TCT GGC GGA GGT GGC AGC GGC GGT GGC GGA TCC CAG TCT GCC CTG ACT CAG CCT GC-3') (SEQ ID NO:49); sPLHV$_\lambda$-3 (5'-TCC TCA GGC GGC GGC GGC TCT GGC GGA GGT GGC AGC GGC GGT GGC GGA TCC TCC TAT GTG CTG ACT CAG CCA CC-3') (SEQ ID NO:50); sPLHV$_\lambda$-4 (5'-TCC TCA GGC GGC GGC GGC TCT GGC GGA GGT GGC AGC GGC GGT GGC GGA TCC TCT TCT GAG CTG ACT CAG GAC CC-3') (SEQ ID NO:51); sPLHV$_\lambda$-5 (5'-TCC TCA GGC GGC GGC GGC TCT GGC GGA GGT GGC AGC GGC GGT GGC GGA TCC CAC GTT ATA CTG ACT CAA CCG CC-3') (SEQ ID NO:52); sPLHV$_\lambda$-6 (5'-TCC TCA GGC GGC GGC GGC TCT GGC GGA GGT GGC AGC GGC GGT GGC GGA TCC CAG GCT GTG CTC ACT CAG CCG TC-3') (SEQ ID NO:53); and sPLHV$_\lambda$-7 (5'-TCC TCA GGC GGC GGC GGC GGC TCT GGC GGA GGT GGC AGC GGC GGT GGC GGA TCC AAT TTT ATG CTG ACT CAG CCC CA-3') (SEQ ID NO:54). After briefly centrifuging, Taq DNA polymerase (3.5 U) and dNTPs (1.5 mM each for dATP, dCTP, dGTP and dTTP) were added to form promoter-linked double stranded cDNAs at 52° C. for 3 min and then 68° C. for 10 min. An in vitro transcription (IVT) reaction (40 µl) was prepared, containing 4 µl of 10×buffer, the above reaction mixture, rNTPs (2 mM each for ATP, GTP, CTP and UTP), and T7 RNA polymerase (160 U). After a 1 hour incubation at 37° C., the antisense amplified $V_\lambda$ RNA transcripts were directly used for making the double stranded $V_\lambda$ DNA homologs. The antisense RNA transcripts were purified and collected by a microcon-50 microconcentrater filter and then subjected reverse transcription (RT) by mixing with a reaction admixture (20 µl) comprising 2 µl of 10× buffer, 1 µM sense peptide linker-linked $HV_\lambda$ primers of above, dNTPs (1.5 mM each for dATP, dGTP, dCTP and dTTP) and RNase inhibitors (20 U). After M-MuLV reverse transcriptase (40 U) was added, the reaction was incubated at 42° C. for 1 hour and shifted to 52° C. for another 15 min. The sense orientation first strand cDNAs so obtained were collected by a microcon-50 microconcentrater filter. The resulting purified sense orientation first strand cDNAs were denatured from the antisense RNA transcripts by denaturation at 94° C. for 3 min and then instantly mixed with 1 µM of the T7-linked antisense $HJ_\lambda$ primers mixture as described above. After briefly centrifuging, Taq DNA polymerase (3.5 U) and dNTPs (1.5 mM each for dATP, dCTP, dGTP and dTTP) were added and the mixture incubated at 52° C. for 3 min and then 68° C. for 10 min to form promoter-linked double stranded cDNAs.

The resulting ds $V_\lambda$ DNA homologs can be further transcriptionally amplified by repeating the IVT using the T7 RNA polymerase. The resulting ds $V_\lambda$ DNA homologs can be the templates for further cloning and processing into either an in vivo expression vector or an in vitro transcription/translation unit mixture such as the PROfusion or ribosome display method.

In the case of making the $scF_\nu$ antibody, the $V_\lambda$ DNA homologs made as discussed above can be used as the template for making single stranded antisense $V_\lambda$ sequences by using a single antisense primer sequence, such as the antisense Sfi-scF$_\nu$ primer, 5'-GTC CTC GTC GAC TGG AAT TCG GCC CCC GAG GCC AC-3') (SEQ ID NO:56) (Table 4) in a primer extension reaction. Briefly, the $V_\lambda$ DNA homologs (20 ng) made above were added to an admixture of 1 µM of the above antisense primer, Taq DNA polymerase (3.5 U) and dNTPs (1.5 mM each for dATP, dCTP, dGTP and dTTP), the mixture was denatured at 94° C. for 5 min., then followed by five cycles of 1 min at 94° C., 1 min at 60° C. and 1.5 min at 72° C. The single stranded sense $V_\lambda$ DNA sequences were then used in an overlapping strand extension reaction with the single stranded sense $V_H$ DNA sequences, made above, as follows.

Linkage of $V_H$ and $V_L$ into a single chain $V_H+V_L$ sequence was accomplished using the single stranded sense $V_H$ DNA sequences made above and the single stranded sense $V_L$ ($V_K$ and $V_\lambda$) made above that were constructed with an overlapping linker sequence that are complementary for hybridization annealing. The annealed two single stranded sequences can be extended to form ds $V_H+V_L$ single chain DNA sequences as the $scF_\nu$ DNA homologs (see FIG. 10) readily for further cloning and expression applications. Briefly, single stranded sense $V_H$ DNA sequences (20 ng) made above were mixed with 20 ng of single stranded antisense $V_L$ (10 ng of $V_K$ made above and 10 ng of $V_\lambda$ made above) and added to a solution containing Taq DNA polymerase (3.5 U) and dNTPs (1.5 mM each for dATP, dCTP, dGTP and dTTP), with incubation at 52° C. for 3 min and then 68° C. for 10 min to form ds DNAs. The resulting ds single chain $V_H$-(Gly$_4$Ser)$_3$-$V_L$ were used in the following cloning steps for making an $scF_\nu$ antibody phage display library.

The $scF_\nu$ DNA sequences can be further cloned into an appropriate expression vector or an in vitro transcription/translation reaction mixture. Appropriate restriction site(s) can be added to the flanking sequences for the single chain $scF_\nu$ sequences. In that case, the Sfi cutting site was selected for cloning into a pCGMT9 phage vector as described by Gao, et al (1999) (Proc. Natl. Acad. Sci. USA 96, 6035-6230), see FIG. 10. Briefly, the ds $scF_\nu$ sequences made above containing the Sfi restriction sites at both ends were digested with Sfi and readily ligated with the pCGMT9 vector predigested with Sfi. The $scF_\nu$ antibody can be expressed and the $scF_\nu$ phage library so made can be screened for preselected antigen-binding activities according to the description of Gao et al. (1999) (Proc. Natl. Acad. Sci. USA 96, 6035-6230).

Example 11

Screen of Human Antibody Phage Library for Preselected Antigen Binding Activity

To identify and to isolate the individual phage clones containing the human antibody DNA homologs that code for an antigen binding protein, the human antibody phage library made as in Examples 6 to 10 was titered first and then plated onto agar plates. Replica filter lifts were generated and screened against preselected antigen-binding activity according to the manufacturer instruction manual from Stratagene (La Jolla, Calif.).

The titre of the human antibody expression library prepared according to Examples 6 to 10 was determined using methods well known to one skilled in the art and detailed in the instruction manual from Stratagene (La Jolla, Calif.).

The screening of phage libraries for antigen binding is well known in the art. Briefly, the phage plaque nitrocellulose filter lifts of the expressed human antibody in a phage display library were screened against $^{125}$I-labeled BSA (bovine serum albumin) conjugated with a preselected ligand at a density of approximately 30,000 plaques per 150 mm plate. The primary phage plagues identified and isolated were subjected to a secondary screening.

Screening employed standard plaque lift methods well known in the art and performed following the instruction manual from Stratagene (La Jolla, Calif.). Typically, the XL1 Blue cells infected with phage were incubated on 150 mm plates for 4 h at 37° C., protein expression induced by overlay with nitrocellulose filters soaked in 10 mM isopropyl thiogalactoside (IPTG) and the plates incubated at 25° C. for 8 hours. Duplicate filters were obtained during a second incubation employing the same conditions. Filters were then blocked in a solution of 1% BSA in PBS for 1 hour before incubation with rocking at 25° C. for 1 hour with a solution of $^{125}$I-labeled BSA conjugated to ligand ($2\times10^6$ cpm ml$^{-1}$; BSA concentration at 0.1 M; approximately 15 ligand molecules per BSA molecule) in 1% BSA/PBS. Background was reduced by pre-centrifligation of stock radiolabeled BSA solution at 100,000 g for 15 min and pre-incubation of solutions with plaque lifts from plates containing bacteria infected with a phage having no insert. After labeling, filters were washed repeatedly with PBS/0.05% Tween 20 before development of autoradiographs overnight.

Example 12

In Vitro Antibody Expression Libraries Constructed in an In Vitro Transcription/Translation Unit The $V_H$, $V_L$ or $V_H+V_L$ gene repertoire can be expressed in an in vitro transcription and translation system such as the PROfusion system described in the U.S. Pat. No. 6,214,553 to Szostak, et al., Feb. 5, 1999 or in an in vitro transcription and translation system such as the ribosome display system as described in the PCT patent application WO 91/05058 by Glenn Kawasaki.

Example 13

In Vitro Antibody Selection Against Specific Antigen Binding Activity From In Vitro Antibody Expression Libraries.

The expressed antibody of $V_H$, $V_L$ or $V_H+V_L$ gene repertoire in an in vitro transcription and translation system such as the PROfusion system or the ribosome display system can be identified and isolated as described in the U.S. Pat. No. 6,214,553 to Szostak, et al. or as described in the PCT patent application WO 91/05058 by Glenn Kawasaki.

REFERENCES

All references cited herein and herein incorporated by reference in entirety.

Bird et al.: *Science*, 242:423-426 (1988).
Chomczynski et al.: *Anal Biochem.*, 162:156-159 (1987)
Compton, J.: *Nature* 350: 91-92 (1991).
DiLella et al.: *Methods In Enzymol.*, 152:199-212 (1987).
Eberwine et al.: *Proc. Natl. Acad. Sci. USA* 89: 3010-3014 (1992).
Frischauf: *Methods In Enzymol.*, 152:183-190 (1987).
Frischauf: *Methods In Enzymol.*, 152:190-199 (1987).
Gao C. S. et al.: *Proc. Natl. Acad. Sci. USA* 96, 6025-6030 (1999).
Haard H. J. D. et al.: *J. Biol. Chem.* 274, 18218-18230 (1999).
Haidaris, C. G. et al.: *J. Immunol. Methods* 257, 185-202 (2001).
Herrmann et al.: *Methods In Enzymol.*, 152:180-183, (1987).
Marks, J. D. et al.: *Eur. J. Immunol.* 21, 985-991 (1991).
Marks, J. D. et al.: *J. Mol. Biol.* 222, 581-597 (1991).
Methods in Enzymology, Volume 155, pp. 335-350 (1987).
Murakawa et al.: *DNA* 7:287-295 (1988).
Sambrook et. al. "*Molecular Cloning, 2nd Edition*",Cold Spring Harbor Laboratory Press, pp8.11-8.19 (1989).
Lin S.-L. et al.: *Nucleic Acid Res.* 27: 4585-4589 (1999).
Welschof, M. et al.: *J. Immunol. Methods*, 179, 203-214 (1995).
U.S. Pat. Nos. 4,683,195, 4,683,202, 4,800,159, 4,965,188 to Mullis et al.
U.S. Pat. No. 4,704,692 issued to Ladner.
U.S. Pat. No. 5,130,238 issued to Malek et al.
U.S. Pat. Nos. 5,409,818; 5,466,586; 5,554,517 and 6,063,603 issued to Davey et al.
U.S. Pat. No. 5,514,545 issued to Eberwine et.al.
U.S. Pat. No. 5,817,465 issued to Mallet et.al.
U.S. Pat. No. 5,888,779 issued to Kacian et.al.
U.S. Pat. No. 5,942,391 issued to Zhang et al.
U.S. Pat. No. 6,197,554 issued to Lin et.al.
U.S. Pat. No. 6,214,553 issued to Szostak et al.
U.S. Pat. No. 6,214,587.
U.S. Pat. No. 6,287,824 issued to Lizardi.
U.S. Pat. No. 6,291,158 issued to Winter et al.
U.S. Pat. No. 6,291,161 issued to Lerner et al.
EPO Application No. 88113948.9 by Davey & Malek.
EPO Application No. 89313154 by Kacian & Fultz;
Europe Patent Publication 320,308.
PCT patent application WO 91/05058 by Glenn Kawasaki
WO 88/10315 by Gingeras et al.
WO 89/1050 by Burg et al.
WO 91/02818 by Malek et al.

The ideas, embodiments and examples presented herein provide a better in vitro RNA transcription-based method and approach to amplification and cloning of the diverse antibody repertoire and the expression therefrom. The foregoing is intended as illustrative of the present invention but not limiting. Numerous variations and modifications can be effected without departing from the true spirit and scope of the invention.

I claim:

1. A process for isolating a nucleic acid encoding a protein that binds to a target antigen, comprising:

(a) exposing a plurality of nucleic acids encoding a plurality of different proteins that bind a plurality of different antigens to a plurality of promoter-linked primers in a single reaction mixture under conditions suitable to produce a DNA comprising a nucleic acid that functions as an RNA polymerase promoter, wherein said promoter-linked primers consist of an RNA polymerase promoter sequence and a gene-specific sequence;

(b) transcribing said DNA of step (a) with a suitable RNA polymerase to produce plural RNAs;

(c) reverse transcribing said plural RNAs to produce plural reverse transcribed DNA;

(d) exposing said plural reverse transcribed DNA to said plurality of promoter-linked primers under conditions suitable to produce additional DNA comprising nucleic acid that functions as an RNA polymerase promoter;

(e) transcribing said additional DNA of step (d) with a suitable RNA polymerase to produce additional plural RNAs;

(f) cloning said DNA, RNA or functional parts thereof under conditions that enable expression of said protein;

(g) expressing proteins encoded by said cloned DNA or RNA of step (f); and (h) screening said expressed proteins with said target antigen to identify a protein that specifically binds thereto, thereby identifying a nucleic acid encoding a protein that binds to said antigen.

2. The process of claim 1, wherein said nucleic acid encoding said protein is an RNA.

3. The process of claim 1, wherein the identified protein comprises $V_H$, $V_L$, or a combination thereof.

4. The process of claim 3, wherein the identified protein comprises $V_h$ and $V_L$.

5. The process of claim 4, wherein the identified protein further comprises a linker molecule between said $V_H$ and said $V_L$.

6. The process of claim 1 wherein said conditions that enable expression comprise a vector in a cell, an in vitro transcription/translation reaction mixture or a combination of both.

7. The process of claim 1 further comprising, after step (a) and before step (f), modifying said RNAs of step (b) or (e), or said DNAs of step (a), (c), or (d) to yield additional proteins that bind antigen.

8. The process of claim 7, wherein said modifying is by mutagenesis.

9. A process for making a library of proteins that bind to antigens, comprising:
   (a) exposing a plurality of nucleic acids encoding different proteins that bind different antigens to a plurality of promoter-linked primers in a single reaction mixture under conditions suitable to produce a DNA comprising a nucleic acid that functions as an RNA polymerase promoter, wherein said promoter-linked primers consist of an RNA polymerase promoter sequence and a gene-specific sequence;
   (b) transcribing the DNA sequence of step (a) with a suitable RNA polymerase to produce plural RNAs;
   (c) reverse transcribing said plural RNAs to produce plural reverse transcribed DNA;
   (d) exposing said plural reverse transcribed DNA to said plurality of promoter-linked primers under conditions suitable to produce additional DNA comprising nucleic acid that functions as an RNA polymerase promoter;
   (e) transcribing said additional DNA of step (d) with a suitable RNA polymerase to produce additional plural RNAs;
   (f) cloning said DNA sequence or said RNA sequence or functional parts thereof in an expression system; and
   (g) expressing proteins encoded by the cloned DNA sequence or RNA sequence or fragment thereof to form a library of expressed proteins capable of binding different antigens.

10. The process of claim 9 further comprising screening the expressed proteins with an antigen to identify a protein that binds to said antigen.

11. The process of claim 9 wherein said nucleic acids are RNA.

12. The process of claim 9 wherein said proteins are selected from the group consisting of $V_H$, $V_L$, and combinations thereof.

13. The process of claim 9 wherein said proteins comprise $V_H$ and $V_L$, said proteins further comprising a linker bonded between the $V_H$ and the $V_L$.

14. The process of claim 9 wherein said expression system is an expression system comprising a vector and a host cell, an in vitro transcription and translation expression system or a combination thereof, and wherein said proteins are expressed using a vector and a host cell, an in vitro transcription and translation expression system or a combination thereof.

15. The process of claim 9 further comprising, after step (a) and before step (f), modifying said RNAs of step (b) or (e), or said DNAs of step (a), (c), or (d) to yield additional proteins that bind antigens.

16. The process of claim 15, wherein said modifying is by mutagenesis.

17. The process of claim 1, further comprising repeating steps (c), (d) and (e) with said additional plural RNAs to produce plural copies of said DNA sequence or said RNA sequence.

18. The process of claim 9, further comprising repeating steps (c), (d) and (e) with said additional plural RNAs to produce plural copies of said DNA sequence or said RNA sequence.

* * * * *